United States Patent
Kim et al.

(10) Patent No.: US 9,296,695 B2
(45) Date of Patent: Mar. 29, 2016

(54) BIPYRIDINE-BASED COMPOUND AND ORGANIC LIGHT EMITTING DIODE EMPLOYING ORGANIC LAYER COMPRISING THE SAME

(75) Inventors: Hee-Yeon Kim, Suwon-si (KR); Seung-Gak Yang, Suwon-si (KR); Jun-Han Shin, Suwon-si (KR); Jae-Yong Lee, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1010 days.

(21) Appl. No.: 12/423,694

(22) Filed: Apr. 14, 2009

(65) Prior Publication Data
US 2009/0256473 A1 Oct. 15, 2009

(30) Foreign Application Priority Data
Apr. 15, 2008 (KR) .......................... 10-2008-0034685

(51) Int. Cl.
| | | |
|---|---|---|
| H01L 51/50 | (2006.01) |
| C07D 213/22 | (2006.01) |
| C09K 11/06 | (2006.01) |
| H01L 51/00 | (2006.01) |

(52) U.S. Cl.
CPC .............. *C07D 213/22* (2013.01); *C09K 11/06* (2013.01); *H01L 51/0054* (2013.01); *H01L 51/0067* (2013.01); *C09K 2211/1007* (2013.01); *C09K 2211/1011* (2013.01); *C09K 2211/1029* (2013.01)

(58) Field of Classification Search
USPC ....................... 428/690, 917; 257/40, E51.05, 257/E51.026, E51.32; 313/504, 505, 506; 548/440, 418; 544/234
See application file for complete search history.

(56) References Cited

U.S. PATENT DOCUMENTS

| | | | |
|---|---|---|---|
| 6,559,256 B2 | 5/2003 | Holmes et al. | |
| 7,994,316 B2* | 8/2011 | Yamakawa et al. | ........... 544/180 |
| 2004/0086745 A1 | 5/2004 | Iwakuma et al. | |
| 2006/0003184 A1 | 1/2006 | Hatwar et al. | |
| 2006/0019116 A1 | 1/2006 | Conley et al. | |
| 2006/0186797 A1* | 8/2006 | Nishiyama et al. | ........... 313/504 |
| 2007/0176544 A1 | 8/2007 | Koike et al. | |
| 2008/0111473 A1 | 5/2008 | Kawamura et al. | |
| 2009/0134780 A1 | 5/2009 | Ono et al. | |

FOREIGN PATENT DOCUMENTS

| | | |
|---|---|---|
| EP | 0 061 128 A1 | 9/1982 |
| EP | 0 451 585 A2 | 10/1991 |
| EP | 1 231 207 A1 | 8/2002 |

(Continued)

OTHER PUBLICATIONS

Extended European Search Report dated Jul. 21, 2009, in corresponding European Patent Application No. 09251099.9, listing the cited references in this IDS.

(Continued)

*Primary Examiner* — Gregory Clark
(74) *Attorney, Agent, or Firm* — Lewis Roca Rothgerber Christie LLP

(57) ABSTRACT

The invention is directed to bipyridine-based compound and organic light emitting diodes (OLED) including organic layers having the bipyridine-based compound. OLEDs including organic layers having the bipyridine-based compounds can have low driving voltages, high current densities, high efficiencies and long lifetimes.

14 Claims, 2 Drawing Sheets

(56) References Cited

FOREIGN PATENT DOCUMENTS

| | | | | |
|---|---|---|---|---|
| EP | 1 690 847 A1 | 8/2006 | | |
| JP | 4-234849 | 8/1992 | | |
| JP | 2003-336043 | * 11/2003 | ............. | C09K 11/06 |
| JP | 2003-336043 A | 11/2003 | | |
| JP | 2004-2297 | 1/2004 | | |
| JP | 2005-317297 A | 11/2005 | | |
| JP | 2006-135155 | * 5/2006 | ............. | H01L 51/50 |
| KR | 10-2004-0094842 | 11/2004 | | |
| KR | 10-2006-0122622 A | 11/2006 | | |
| KR | 10-2007-0033390 A | 3/2007 | | |
| KR | 10-2007-0079022 A | 8/2007 | | |
| KR | 10-2007-0088728 A | 8/2007 | | |
| WO | WO 2007/029696 A1 | 3/2007 | | |

OTHER PUBLICATIONS

Krohnke, Fritz, "The Specific Synthesis of Pyridines and Oligopyridines", Synthesis, Stuttgart, DE, Jan. 1, 1976, pp. 1-24, XP-002438390.

KIPO Registration Determination Certificate dated Jul. 29, 2011, for Korean priority Patent application 10-2008-0034685, noting listed reference in this IDS, as well as JP 2005-317297, previously submitted in an IDS dated Aug. 25, 2009, 5 pages.

Japanese Office action dated Mar. 21, 2012 for corresponding Japanese Patent Application No. 2009-097935, 2pp.

* cited by examiner

BIPYRIDINE-BASED COMPOUND AND ORGANIC LIGHT EMITTING DIODE EMPLOYING ORGANIC LAYER COMPRISING THE SAME

CROSS-REFERENCE TO RELATED PATENT APPLICATION

This application claims priority to and the benefit of Korean Patent Application No. 10-2008-0034685, filed on Apr. 15, 2008 in the Korean Intellectual Property Office, the entire content of which is incorporated herein by reference.

BACKGROUND OF THE INVENTION

1. Field of the Invention

The present invention relates to bipyridine-based compounds and organic light emitting diodes (OLED) employing organic layers including the same. More particularly, the invention is directed to bipyridine-based compounds suitable for electron transport layers of OLEDs and to OLEDs employing organic layers including the bipyridine-based compounds.

2. Description of the Related Art

Organic light emitting diodes (OLEDs) are self-emitting devices that realize multiple colors and have wide viewing angles, excellent contrast and quick response. A typical OLED structure includes an anode, a hole transport layer (HTL), an emitting layer (EML), an electron transport layer (ETL) and a cathode sequentially stacked on a substrate. The HTL, EML and ETL are thin films formed of organic compounds. An OLED with such a structure operates by applying a voltage to the anode and cathode, which causes holes injected from the anode to move to the EML via the HTL, and electrons injected from the cathode to move to the EML via the ETL. The holes and electrons recombine in the EML to generate excitons. When the excitons drop from an excited state to a ground state, a fluorescent material in the EML emits light. The material used to form the ETL may be a heteroaromatic compound such as an oxadiazole, a thiadiazole, or the like. However, conventional OLEDs have insufficient driving voltage, current density, efficiency and lifetime characteristics.

SUMMARY OF THE INVENTION

According to embodiments of the present invention, a bipyridine-based compound has excellent electron transporting capability.

In some embodiments of the present invention, an organic light emitting diode employs the bipyridine-based compound and has low driving voltage, high current density, high efficiency and long lifetime.

According to an embodiment of the present invention, a bipyridine-based compound is represented by Formula 1.

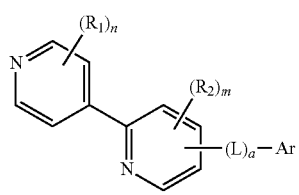

Formula 1

In Formula 1, each of $R_1$ and $R_2$ is independently selected from halogen atoms, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_2$-$C_{30}$ alkenyl groups, substituted and unsubstituted $C_6$-$C_{30}$ aryl groups, and substituted and unsubstituted $C_3$-$C_{30}$ heteroaryl groups. L is selected from substituted and unsubstituted $C_6$-$C_{30}$ arylene groups, and substituted and unsubstituted $C_3$-$C_{30}$ heteroarylene groups. Ar is selected from substituted and unsubstituted $C_6$-$C_{30}$ aryl groups, and substituted and unsubstituted $C_3$-$C_{30}$ heteroaryl groups. Also, n is an integer ranging from 0 to 4, m is an integer ranging from 0 to 3, and a is an integer ranging from 0 to 5.

According to another embodiment of the present invention, an organic light emitting diode (OLED) includes a first electrode, a second electrode, and an organic layer between the first and second electrodes, where the organic layer includes the bipyridine-based compound.

BRIEF DESCRIPTION OF THE DRAWINGS

The above and other features and advantages of the present invention will become more apparent by reference to the following detailed description when considered in conjunction with the attached drawings in which.

DETAILED DESCRIPTION OF THE INVENTION

Figure 1:
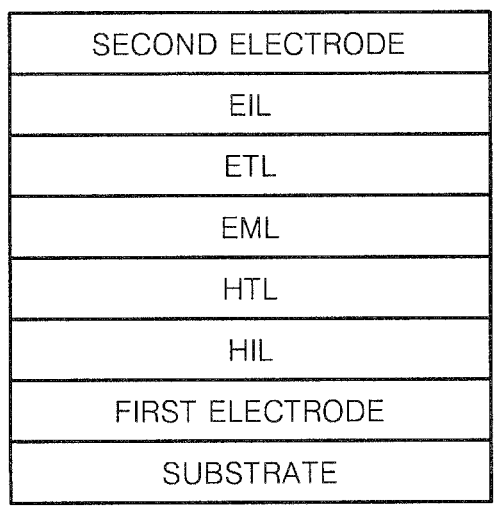
FIG. 1 is a schematic sectional view of an organic light emitting diode (OLED) according to an embodiment of the present invention.

A bipyridine-based compound according to an embodiment of the present invention is represented by Formula 1. The positions of the carbons of the two pyridine rings in the bipyridine-based compound are numbered as shown in Formula 1'.

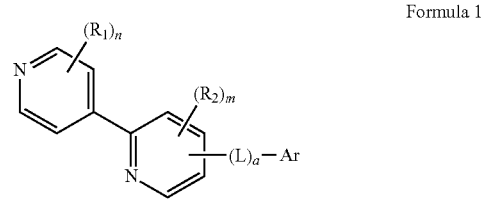

Formula 1

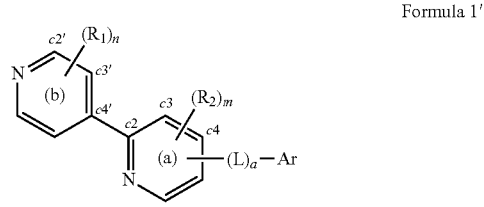

Formula 1'

Referring to Formula 1', if the C4' position of pyridine ring (b) is attached to the C2 position of pyridine ring (a) to which Ar or L is bonded, a compound having unexpectedly good electron transporting capability may be obtained. That is, if N is at the para-position with respect to the C4' carbon of the second pyridine ring (i.e., pyridine ring (b) to which Ar (or L) is not bonded), unexpectedly good electron transporting capabilities (suitable for an organic layer of an organic light emitting diode (OLED)) may be obtained. As described with reference to Formula 1' above, if pyridine ring (a) is bonded to pyridine ring (b), the polarity of the molecule may increase, thereby imparting good electron transporting capabilities.

In Formula 1, each of $R_1$ and $R_2$ may be independently selected from halogen atoms, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_2$-$C_{30}$ alkenyl groups, substituted and unsubstituted $C_6$-$C_{30}$ aryl groups, and substituted and unsubstituted $C_3$-$C_{30}$ heteroaryl groups.

In one embodiment, for example, each of $R_1$ and $R_2$ may be independently selected from halogen atoms, hydroxyl groups, cyano groups, substituted and unsubstituted $C_1$-$C_{10}$ alkyl groups, substituted and unsubstituted $C_2$-$C_{10}$ alkoxy groups, substituted and unsubstituted $C_6$-$C_{12}$ aryl groups, and substituted and unsubstituted $C_3$-$C_{12}$ heteroaryl groups. Nonlimiting examples of suitable substituents for $R_1$ and $R_2$ include halogen atoms, hydroxyl groups, cyano groups, $C_1$-$C_{10}$ alkyl groups, $C_1$-$C_{10}$ haloalkyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

In Formula 1, n and m indicate the number of substituents on pyridine rings (a) and (b), where n is an integer ranging from 0 to 4, and m is an integer ranging from 0 to 3. At least one of n and m may be 0. If both n and m are 0, the pyridine rings (a) and (b) do not include substituents. $R_1$ is as defined above, and when more than one $R_1$ is present, they may be the same or different from each other. Similarly, $R_2$ is as defined above, and when more than one $R_2$ is present, they may be the same or different from each other.

In Formula 1, L may be selected from substituted and unsubstituted $C_6$-$C_{30}$ arylene groups, and substituted and unsubstituted $C_3$-$C_{30}$ heteroarylene groups. In one embodiment, for example, L may be selected from substituted and unsubstituted $C_6$-$C_{12}$ arylene groups, and $C_3$-$C_{12}$ heteroarylene groups. In still another embodiment, L may be selected from substituted and unsubstituted $C_6$-$C_{12}$ arylene groups, and at least one of the hydrogen atoms of the $C_6$-$C_{12}$ arylene group may be substituted with a substituent selected from $C_1$-$C_{10}$ alkyl groups (e.g., methyl groups, ethyl groups, and propyl groups), and $C_1$-$C_{10}$ alkoxy groups (e.g., methoxy groups, ethoxy groups, and propoxy groups).

In addition, in Formula 1, a indicates the number of L substituents, and may be 0, 1, 2, 3, 4 or 5. If a is 0, the bipyridyl group is directly bonded to the Ar substituent. In one embodiment, a may be 0, 1 or 2. If a is 2 or greater, the at least two Ls may be the same or different.

In Formula 1, Ar may be selected from substituted and unsubstituted $C_6$-$C_{30}$ aryl groups, and substituted and unsubstituted $C_3$-$C_{30}$ heteroaryl groups. Nonlimiting examples of suitable unsubstituted $C_6$-$C_{30}$ aryl groups or unsubstituted $C_3$-$C_{30}$ heteroaryl groups include phenyl groups, pentalenyl groups, indenyl groups, naphthyl groups, azulenyl groups, heptalenyl groups, indacenyl groups, acenaphthylenyl groups, fluorenyl groups, phenalenyl groups, phenanthrenyl groups, anthracenyl groups, fluoranthrenyl groups, triphenylenyl groups, pyrenyl groups, chrysenyl groups, naphthacenyl groups, picenyl groups, perylenyl groups, pentaphenyl groups, hexacenyl groups, thiophenyl groups, pyrrolyl groups, pyrazolyl groups, pyrazolidinyl groups, imidazolyl groups, imidazolinyl groups, pyrazinyl groups, pyrimidinyl groups, indolyl groups, benzimidazolyl groups, and quinolinyl groups. In one embodiment, for example, the unsubstituted $C_6$-$C_{30}$ aryl groups or unsubstituted $C_3$-$C_{30}$ heteroaryl groups are selected from anthracenyl groups, pyrenyl groups, perylenyl groups, and chrysenyl groups.

In some embodiments, when Ar is a substituted $C_6$-$C_{30}$ aryl group or a substituted $C_3$-$C_{30}$ heteroaryl group, at least one of the hydrogen atoms thereof may be substituted with a substituent selected from halogen atoms, cyano groups, hydroxyl groups, $C_1$-$C_{10}$ alkyl groups, $C_1$-$C_{10}$ alkoxy groups, phenyl groups, phenyl groups substituted with at least one $C_1$-$C_{10}$ alkyl group or at least one $C_6$-$C_{12}$ aryl group, naphthyl groups, naphthyl groups substituted with at least one $C_1$-$C_{10}$ alkyl group or at least one $C_6$-$C_{12}$ aryl group, anthracenyl groups, anthracenyl groups substituted with at least one $C_1$-$C_{10}$ alkyl group or at least one $C_6$-$C_{12}$ aryl group, fluorenyl groups, fluorenyl groups substituted with at least one $C_1$-$C_{10}$ alkyl group or at least one $C_6$-$C_{12}$ aryl group, phenanthrenyl groups, phenanthrenyl groups substituted with at least one $C_1$-$C_{10}$ alkyl group or at least one $C_6$-$C_{12}$ aryl group, pyrenyl groups, pyrenyl groups substituted with at least one $C_1$-$C_{10}$ alkyl group or at least one $C_6$-$C_{12}$ aryl group, fluoranthrenyl groups, and fluoranthrenyl groups substituted with at least one $C_1$-$C_{10}$ alkyl group or at least one $C_6$-$C_{12}$ aryl group.

The bipyridine-based compound according to embodiments of the present invention may be a compound represented by Formulae 2a to 2j below:

Formula 2a

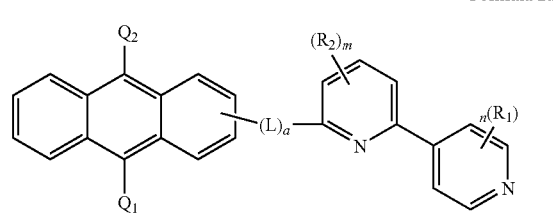

Formula 2b

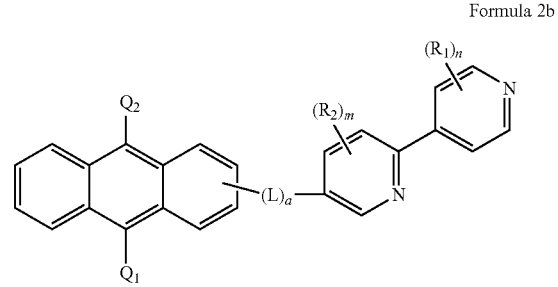

Formula 2c

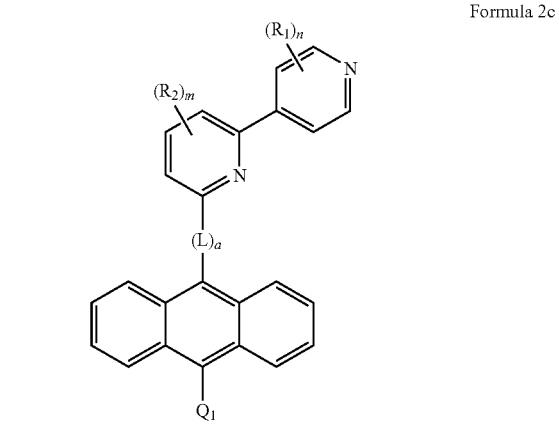

Formula 2d

Formula 2e

Formula 2f

Formula 2g

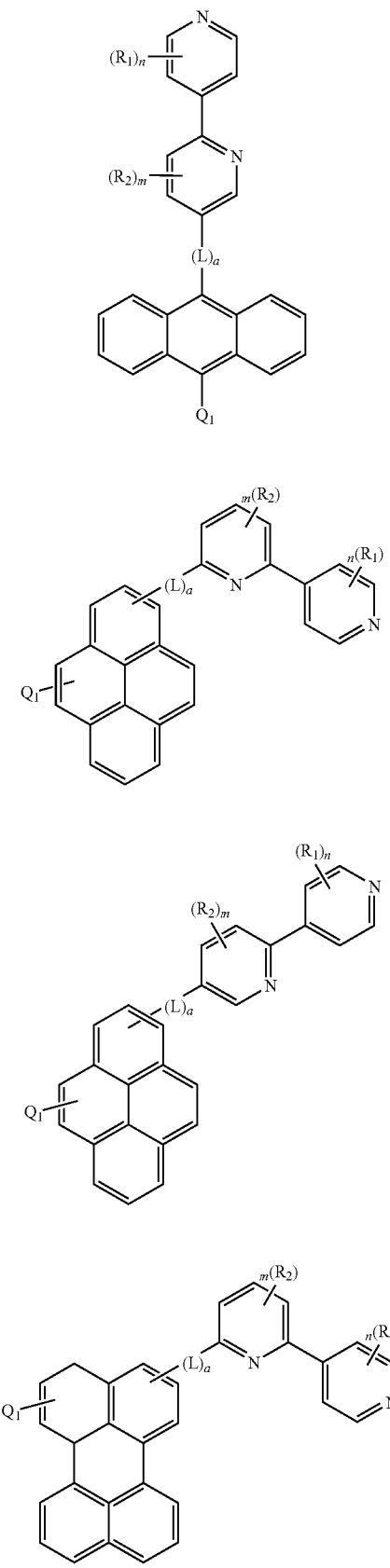

Formula 2h

Formula 2i

Formula 2j

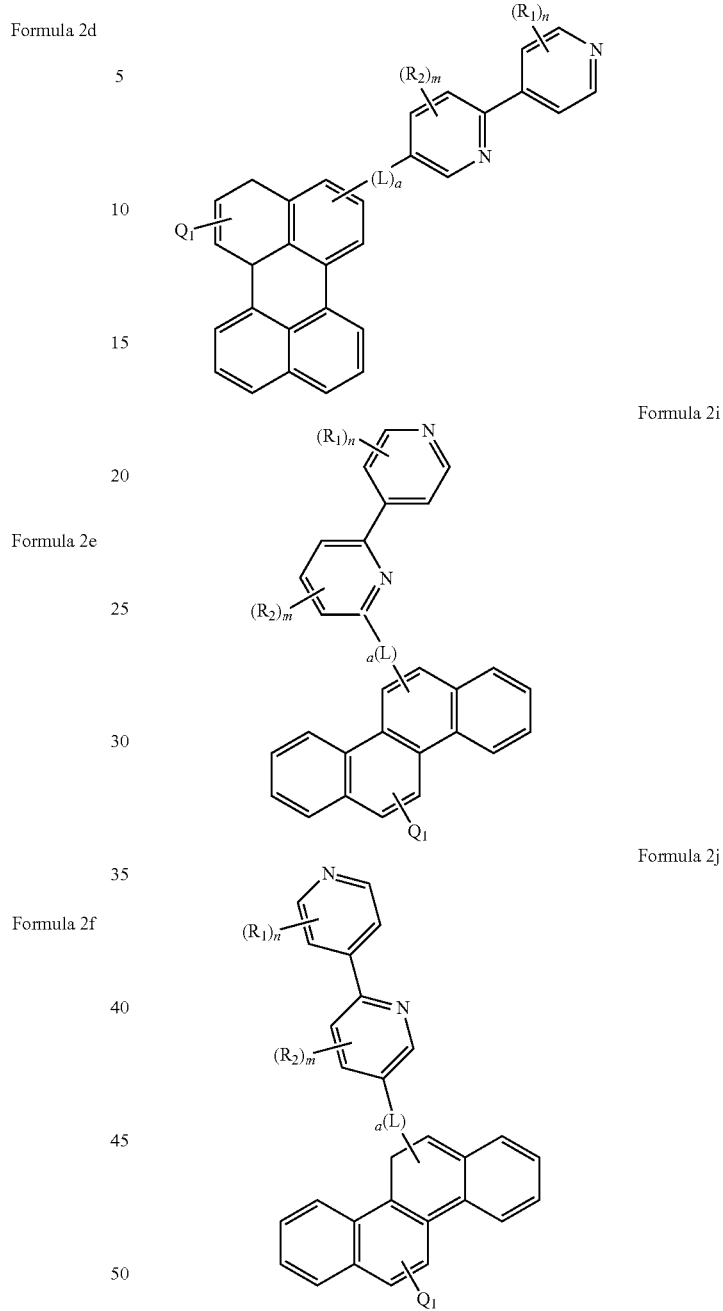

In Formula 2a through 2j, $R_1$, $R_2$, L, a, n and m are as described above with respect to Formula 1. Each of $Q_1$ and $Q_2$ may be independently selected from halogen atoms, cyano groups, hydroxyl groups, $C_1$-$C_{10}$ alkyl groups, $C_1$-$C_{10}$ alkoxy groups, phenyl groups, phenyl groups substituted with at least one $C_1$-$C_{10}$ alkyl group or at least one $C_6$-$C_{12}$ aryl group, naphthyl groups, naphthyl groups substituted with at least one $C_1$-$C_{10}$ alkyl group or at least one $C_6$-$C_{12}$ aryl group, anthracenyl groups, anthracenyl groups substituted with at least one $C_1$-$C_{10}$ alkyl group or at least one $C_6$-$C_{12}$ aryl group, fluorenyl groups, fluorenyl groups substituted with at least one $C_1$-$C_{10}$ alkyl group or at least one $C_6$-$C_{12}$ aryl group, phenanthrenyl groups, phenanthrenyl groups substituted with at least one $C_1$-$C_{10}$ alkyl group or at least one $C_6$-$C_{12}$ aryl group, pyrenyl groups, pyrenyl groups substituted with at least one $C_1$-$C_{10}$ alkyl group or at least one $C_6$-$C_{12}$ aryl group, fluoranthrenyl groups, and fluoranthrenyl groups substituted with at least one $C_1$-$C_{10}$ alkyl group or at least one $C_6$-$C_{12}$ aryl group.

Some nonlimiting examples the bipyridine-based compound according to embodiments of the present invention include the compounds represented by Formulae 3a, 3b, 3e to 3j.

Formula 3a
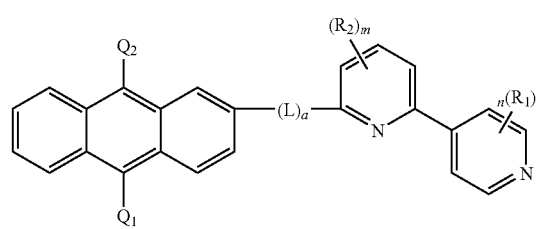

Formula 3b
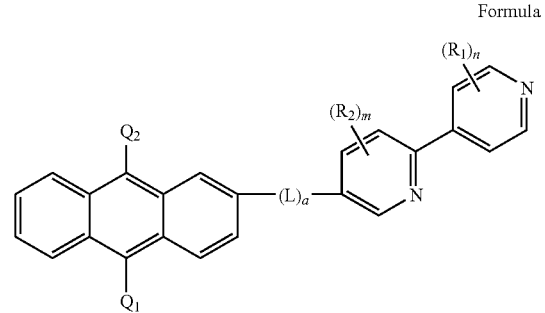

Formula 3e
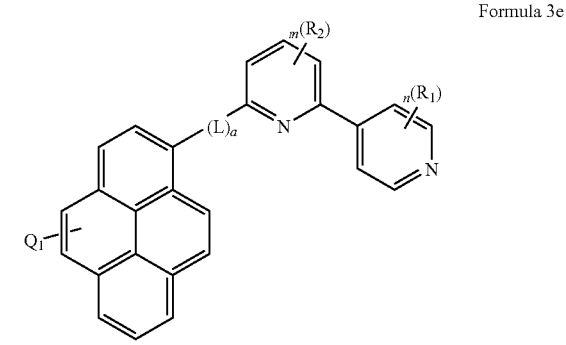

Formula 3f
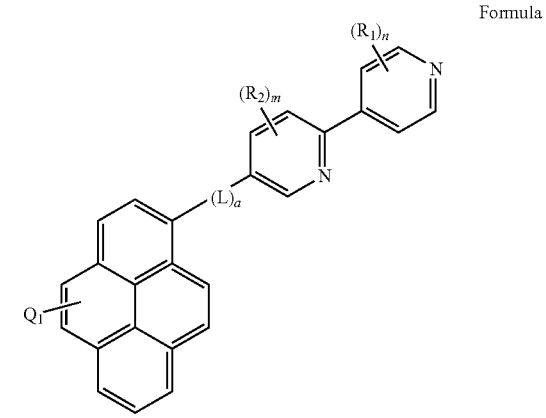

Formula 3g
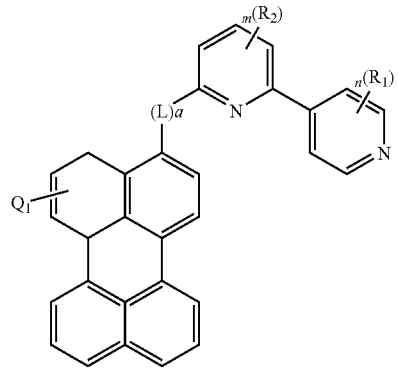

Formula 3h
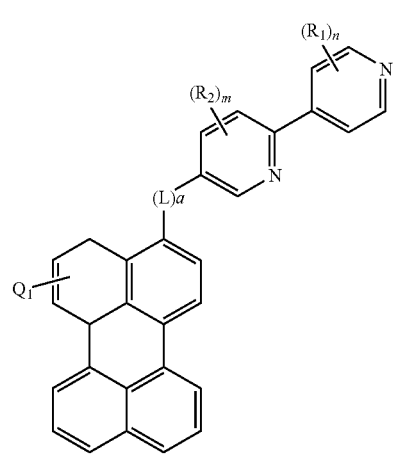

Formula 3i
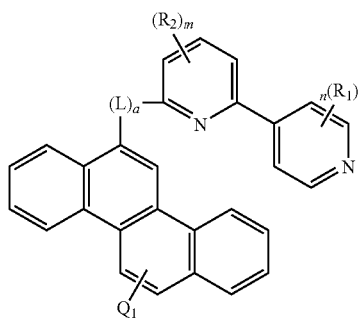

Formula 3j
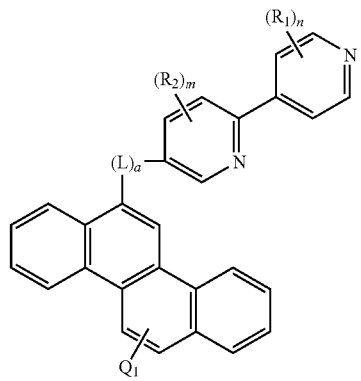

In Formulae 3a, 3b, and 3e through 3j, $R_1$, $R_2$, n, m, L, and a are as defined above with respect to Formula 1, and $Q_1$ and $Q_2$ are as described above with respect to Formula 2a through 2j.

Some nonlimiting examples of suitable substituents for Ar in Formula 1 include those depicted in Formula 4 below.
Formula 4
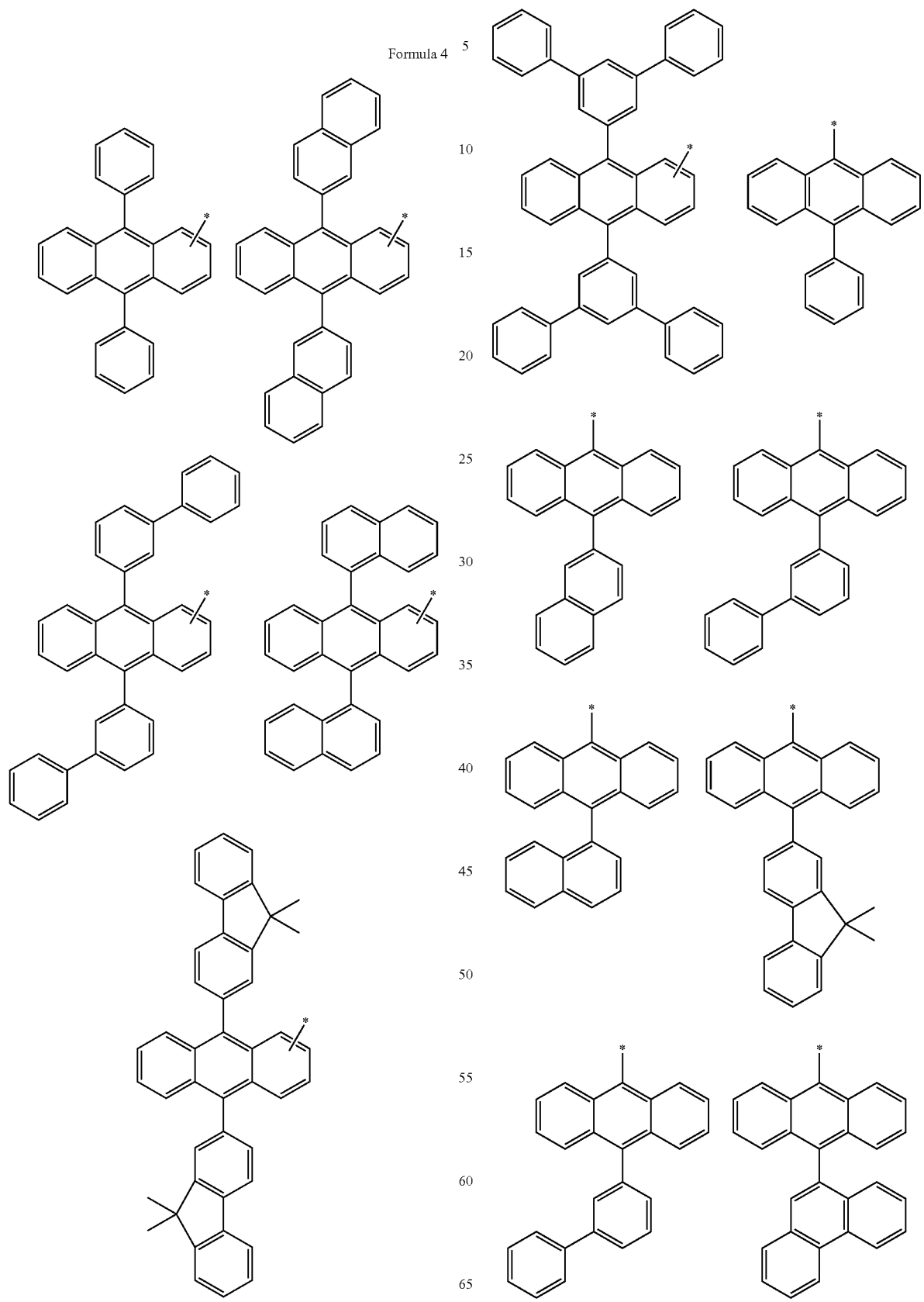

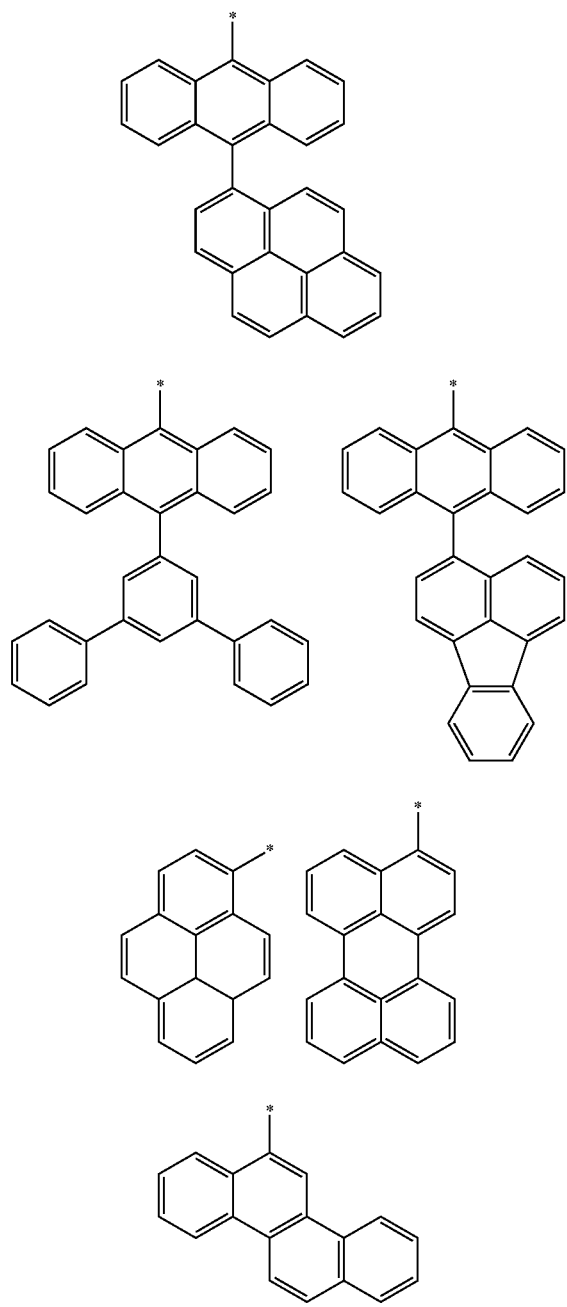

In the compounds depicted in Formula 4, * is a binding site with -(L)$_a$- or a bipyridyl group.

In Formula 1, nonlimiting examples of suitable unsubstituted C$_1$-C$_{30}$ alkyl groups include methyl groups, ethyl groups, propyl groups, isobutyl groups, sec-butyl groups, pentyl groups, iso-amyl groups, and hexyl groups. At least one of the hydrogen atoms in the C$_1$-C$_{30}$ alkyl group may be substituted with a substituent selected from halogen atoms, hydroxyl groups, nitro groups, cyano groups, amino groups, amidino groups, hydrazine groups, hydrazone groups, carboxyl groups and salts thereof, sulfone groups and salts thereof, phosphoric acids and salts thereof, C$_1$-C$_{30}$ alkoxy groups, C$_6$-C$_{30}$ aryl groups, and C$_3$-C$_{30}$ heteroaryl groups.

In Formula 1, nonlimiting examples of suitable unsubstituted C$_1$-C$_{30}$ alkoxy groups include methoxy groups, ethoxy groups, and isopropyloxy groups. At least one of the hydrogen atoms in the C$_1$-C$_{30}$ alkoxy group may be substituted with the same substituents described above with reference to the C$_1$-C$_{30}$ alkyl group.

In Formula 1, the unsubstituted C$_2$-C$_{30}$ alkenyl group is a group including a carbon-carbon double bond at the center or end of the alkyl group. Nonlimiting examples of suitable C$_2$-C$_{30}$ alkenyl groups include ethylene groups, propylene groups, butylene groups, and hexylene groups. At least one of the hydrogen atoms in the C$_2$-C$_{30}$ alkenyl group may be substituted with the same substituents described above with reference to the C$_1$-C$_{30}$ alkyl group.

In Formula 1, the unsubstituted C$_6$-C$_{30}$ aryl group is a carbocyclic aromatic system having from 6 to 30 carbon atoms and including at least one aromatic ring, wherein the at least one ring may be fused to another ring or connected to another ring through a single bond. At least one of the hydrogen atoms in the C$_2$-C$_{30}$ alkenyl group may be substituted with the same substituents described above with reference to the C$_1$-C$_{30}$ alkyl group.

Nonlimiting examples of suitable substituted and unsubstituted C$_6$-C$_{30}$ aryl groups include phenyl groups, C$_1$-C$_{10}$ alkylphenyl groups (e.g., ethylphenyl groups), C$_1$-C$_{10}$ alkylbiphenyl groups (e.g., ethylbiphenyl groups), halophenyl groups (e.g., o-, m- and p-fluorophenyl groups, and dichlorophenyl groups), dicyanophenyl groups, trifluoromethoxyphenyl groups, o-, m- and p-tolyl groups, o-, m- and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (e.g., fluoronaphthyl groups), C$_1$-C$_{10}$ alkylnaphthyl groups (e.g., methylnaphthyl groups), C$_1$-C$_{10}$ alkoxynaphthyl groups (e.g., methoxynaphthyl groups), anthracenyl groups, azulenyl groups, heptalenyl groups, acenaphtylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

In Formula 1, the unsubstituted C$_3$-C$_{30}$ hetero aryl group is an aromatic ring system including at least one carbon ring having at least one heteroatom selected from N, O, P and S. The at least one ring may be fused with another ring or bonded by a single bond. At least one of the hydrogen atoms in the C$_3$-C$_{30}$ hetero aryl group may be substituted with the same substituents described above with reference to the C$_1$-C$_{30}$ alkyl group.

In Formula 1, nonlimiting examples of suitable unsubstituted C$_3$-C$_{30}$ heteroaryl groups include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups.

Nonlimiting examples of suitable bipyridine-based compounds satisfying Formula 1 include Compounds 1 to 27 depicted below.

Compound 1
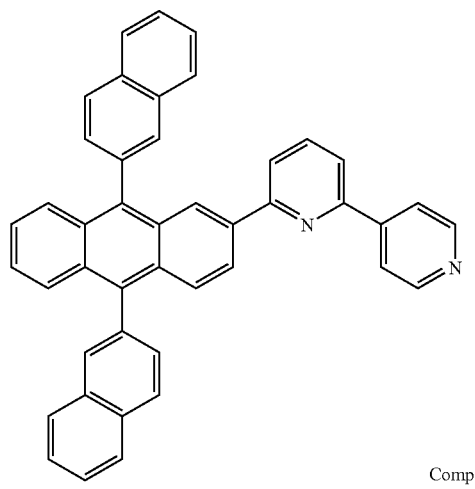
Compound 2
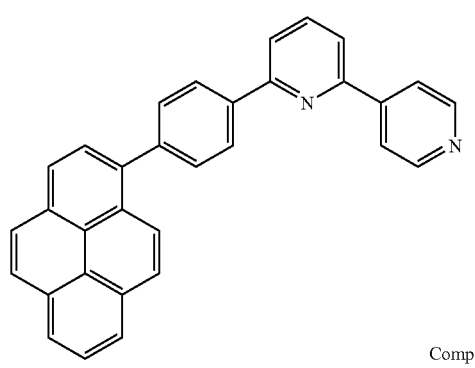
Compound 3
Compound 4
Compound 5
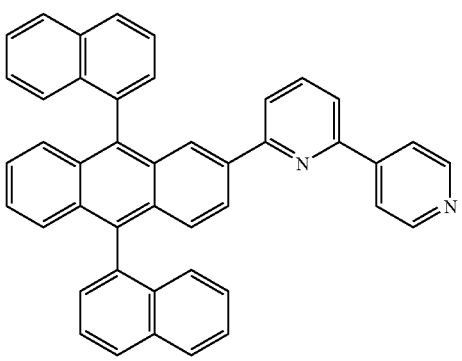
Compound 6
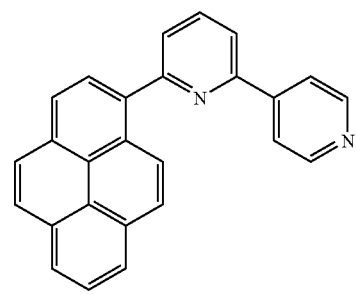
Compound 7
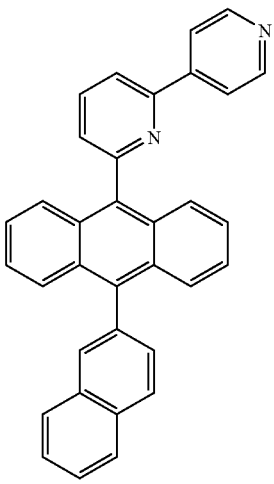

Compound 8
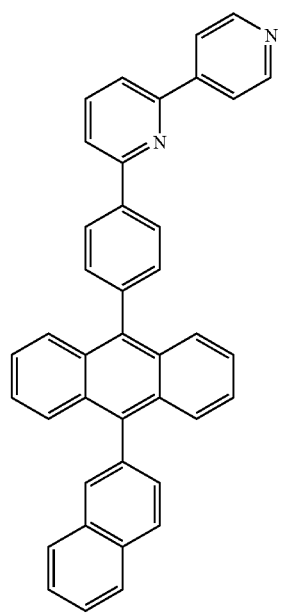
Compound 9
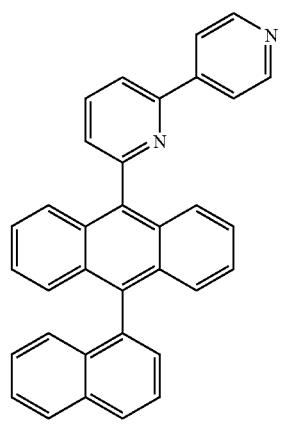
Compound 10
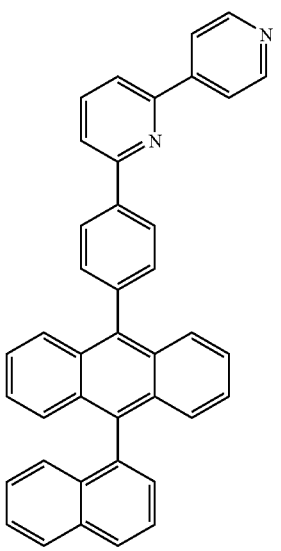
Compound 11
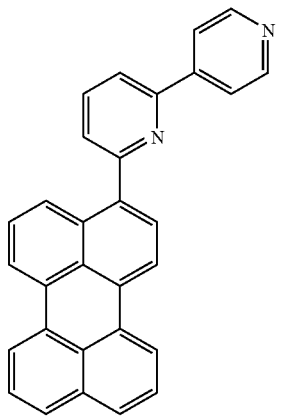
Compound 12
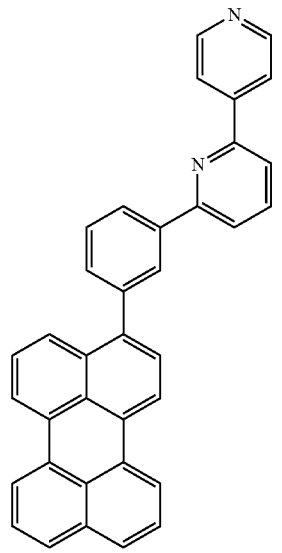
Compound 13
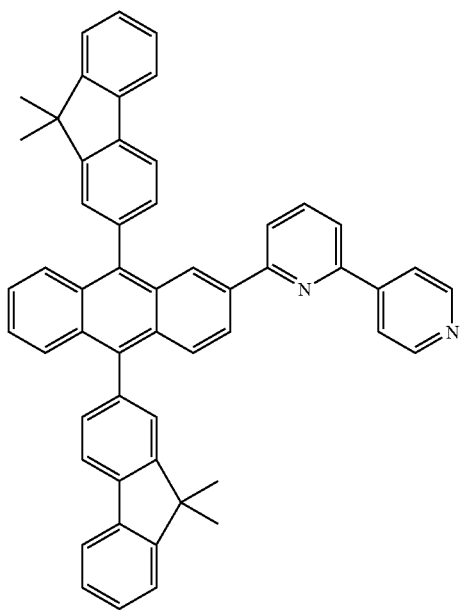

-continued
Compound 14
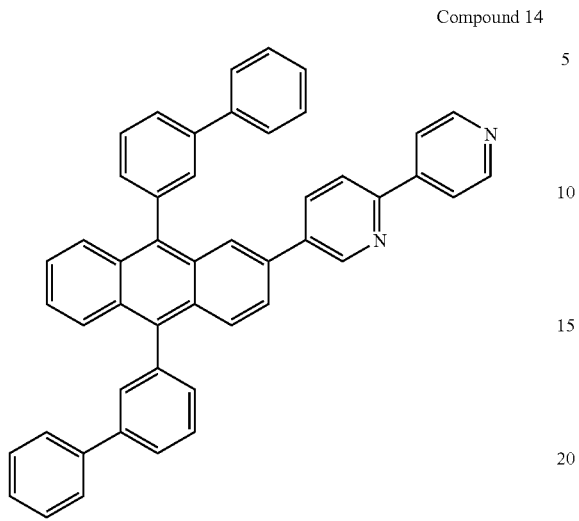
Compound 15
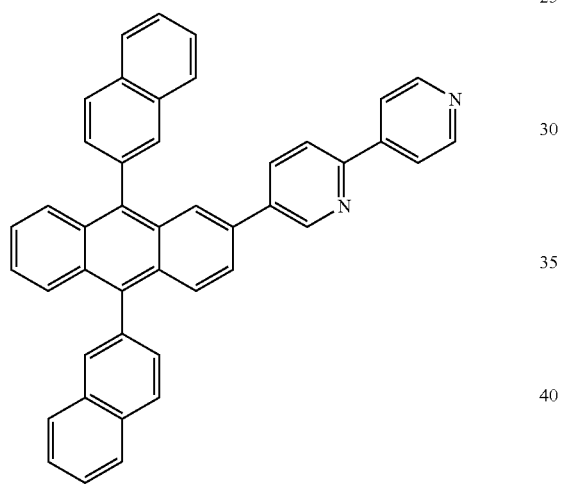
Compound 16
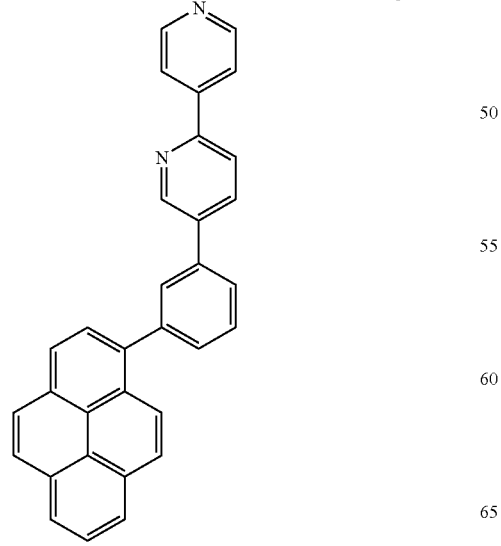
-continued
Compound 17
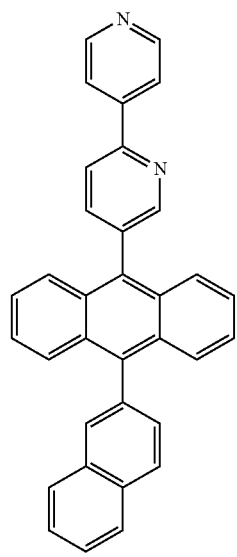
Compound 18
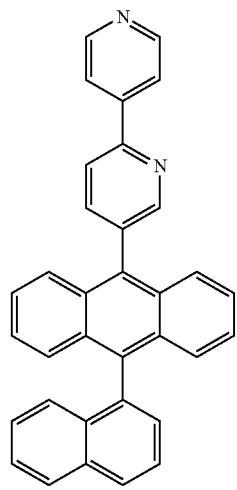
Compound 19
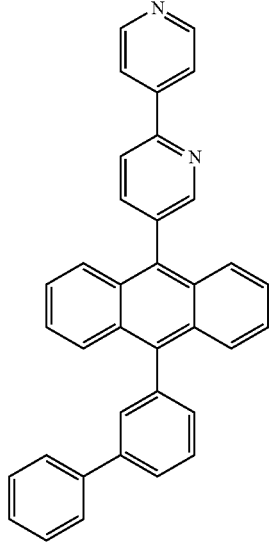

-continued
Compound 20
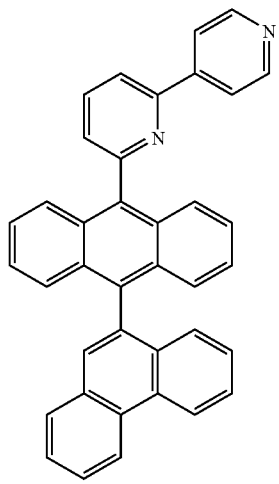
Compound 21
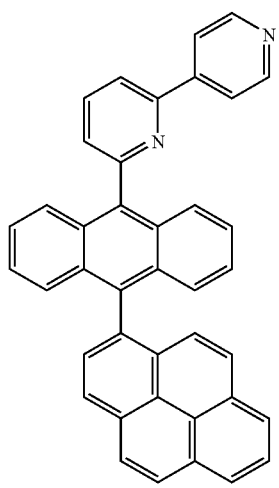
Compound 22
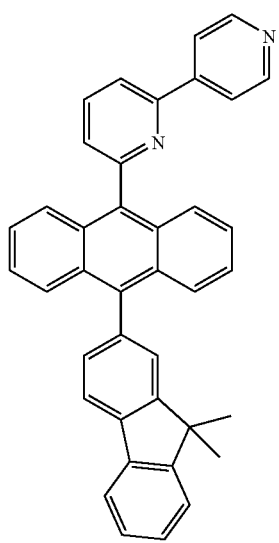
-continued
Compound 23
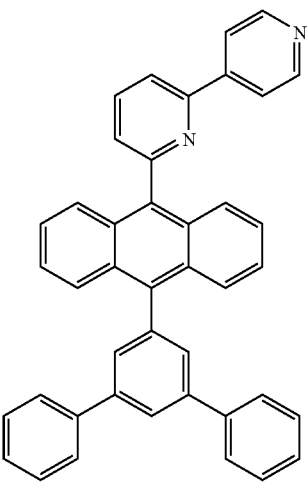
Compound 24
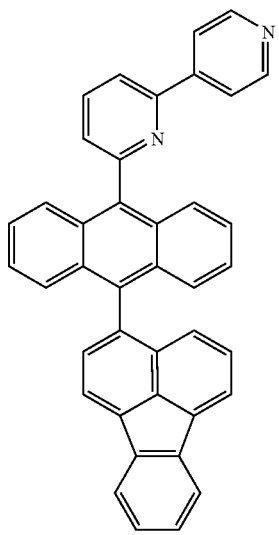
Compound 25
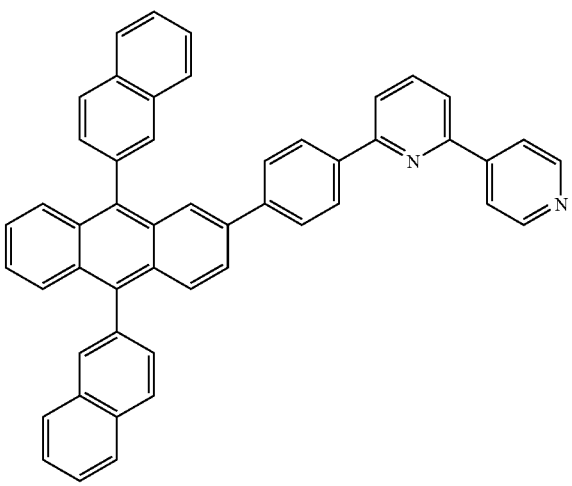

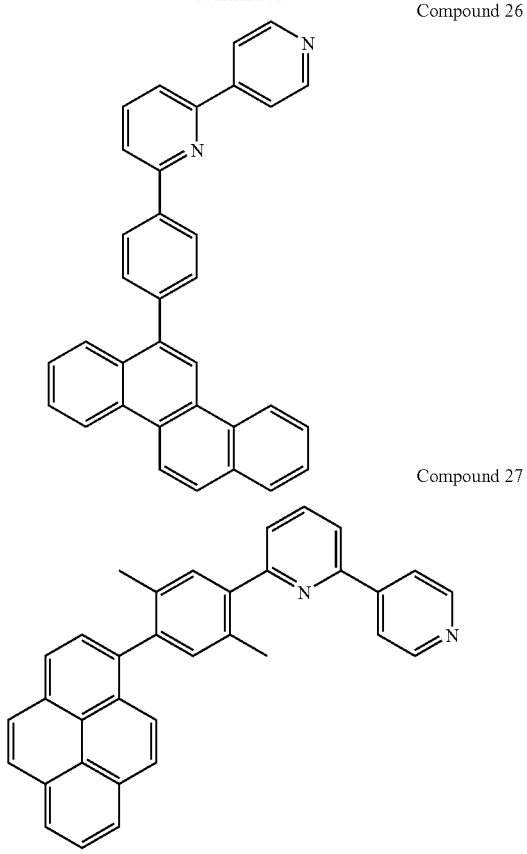

Compound 26

Compound 27

The bipyridine-based compounds represented by Formula 1 may be employed in organic layers of OLEDs. Thus, an OLED according to an embodiment of the present invention includes a first electrode, a second electrode, and an organic layer between the first and second electrodes, where the organic layer includes a bipyridine-based compound represented by Formula 1. The organic layer may be an electron transport layer (ETL). The OLED may further include at least one layer selected from hole injection layers (HILs), hole transport layers (HTLs), electron blocking layers (EBLs), emitting layers (EMLs), hole blocking layers (HBLs), ETLs and electron injection layers (EILs). For example, if the organic layer including a bipyridine-based compound of Formula 1 is an ETL, the OLED may further include a HIL, a HTL, an EML and an EIL. Furthermore, if the EML is formed of a phosphorescent material, the OLED may further include a HBL. The OLED may also have other structures.

FIG. 1 is a schematic sectional view of an OLED according to an embodiment of the present invention. The OLED of FIG. 1 has a first electrode/HIL/HTL/EML/ETL/EIL/second electrode structure. The structure of the OLED is not particularly limited, however, and may be any suitable structure. For example, the OLED may have a first electrode/HIL/HTL/EML/HBL/ETL/second electrode structure, or a first electrode/HIL/HTL/EML/HBL/ETL/EIL/second electrode structure. The ETL may include a compound of Formula 1.

The EML of the OLED may include a red, green, blue or white phosphorescent or fluorescent dopant. The phosphorescent dopant may be an organometallic compound including at least one element selected from Ir, Pt, Os, Ti, Zr, Hf, Eu, Tb and Tm.

A method of manufacturing an OLED according to the present invention will now be described with reference to the OLED illustrated in FIG. 1. First, a first electrode is formed by depositing or sputtering a high work-function material on a substrate. The first electrode can be an anode or a cathode. The substrate, which can be any substrate that is commonly used in OLEDs, may be a glass substrate or a transparent plastic substrate that is easily treated, is waterproof, and has good mechanical strength, thermal stability, transparency, and surface smoothness. The first electrode can be formed of ITO, IZO, $SnO_2$, ZnO, or any highly conductive material, without limitation. The first electrode may be a transparent, semitransparent or reflective electrode.

A HIL can then be formed on the first electrode by vacuum deposition, spin coating, casting, Langmuir Blodgett (LB) deposition, or the like. When the HIL is formed by vacuum deposition, the vacuum deposition conditions may vary according to the compound that is used to form the HIL and the desired structure and thermal properties of the HIL to be formed. In general, however, the vacuum deposition may be performed at a deposition temperature ranging from about 100° C. to about 500° C., under a pressure ranging from about $10^{-8}$ torr to about $10^{-3}$ torr, and at a deposition speed ranging from about 0.01 to about 100 Å/sec.

When the HIL is formed by spin coating, the coating conditions may vary according to the compound that is used to form the HIL and the desired structure and thermal properties of the HIL to be formed. In general, however, the coating speed may range from about 2000 rpm to about 5000 rpm, and the temperature for heat treatment (which is performed to remove solvent after coating) may range from about 80° C. to about 200° C.

The HIL may be formed of any material that is commonly used to form HILs, without limitation. Nonlimiting examples of suitable materials for the HIL include phthalocyanine compounds (such as copperphthalocyanine), star-burst type amine derivatives (such as TCTA (shown below), m-MTDATA (shown below), and m-MTDAPB), soluble and conductive polymers (such as polyaniline/dodecylbenzene-sulfonic acid (Pani/DBSA)), poly(3,4-ethylenedioxythiophene)/poly(4-styrenesulfonate (PEDOT/PSS): polyaniline/camphor sulfonic acid (Pani/CSA), and (polyaniline)/poly(4-styrenesulfonate) (PANI/PSS).

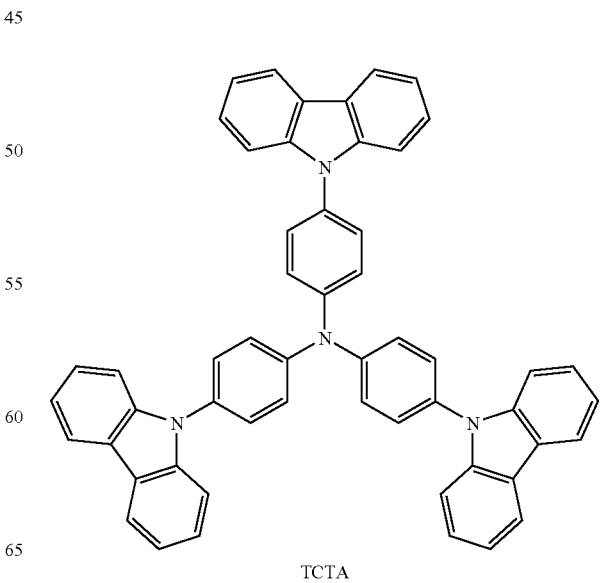

TCTA

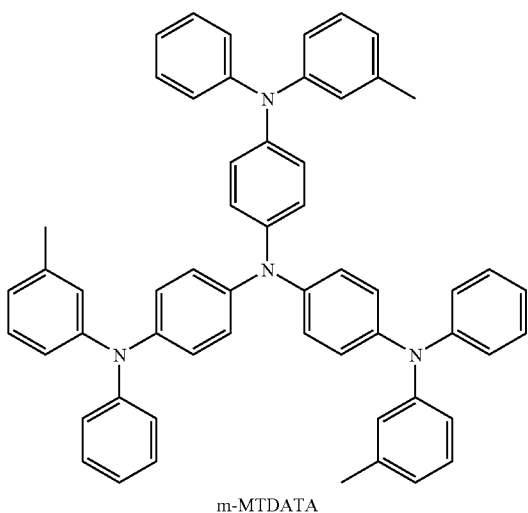

m-MTDATA

The thickness of the HIL may range from about 100 Å to about 10,000 Å. In one embodiment, for example, the thickness of the HIL ranges from about 100 Å to about 1000 Å. When the thickness of the HIL is less than about 100 Å, the hole injecting ability of the HIL may decrease. On the other hand, when the thickness of the HIL is greater than about 10,000 Å, the driving voltage of the OLED may increase.

A hole transport layer (HTL) can be formed on the HIL by vacuum deposition, spin coating, casting, LB deposition, or the like. When the HTL is formed by vacuum deposition or spin coating, the conditions for deposition or coating are similar to those described above with respect to formation of the HIL, although the conditions for deposition and coating may vary according to the material that is used to form the HTL.

The HTL may be formed of any material that is commonly used to form HTLs, without limitation. Nonlimiting examples of suitable materials for the HTL include carbazole derivatives (such as N-phenylcarbazole and polyvinylcarbazole), and amine derivatives having aromatic condensation rings (such as N,N'-bis(3-methylphenyl)-N,N'-diphenyl-[1,1-biphenyl]-4,4'-diamine(TPD), and N,N'-di(naphthalene-1-yl)-N,N'-diphenyl benzydine (α-NPD), both shown below).

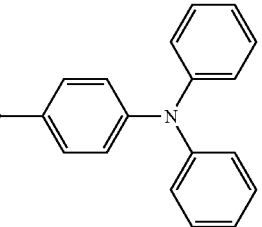

TPD

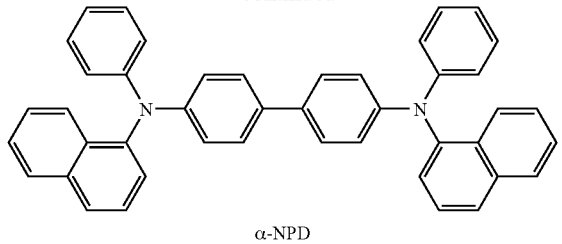

α-NPD

The thickness of the HTL may range from about 50 Å to about 1000 Å. In one embodiment, for example, the thickness ranges from about 100 Å to about 600 Å. When the thickness of the HTL is less than about 50 Å, the hole transporting ability of the HTL may decrease. On the other hand, when the thickness of the HTL is greater than about 1000 Å, the driving voltage of the OLED may increase.

An emissive layer (EML) can be formed on the HTL by vacuum deposition, spin coating, casting, LB deposition, or the like. When the EML is formed by vacuum deposition or spin coating, the conditions for deposition and coating are similar to those described above with respect to the formation of the HIL, although the conditions for deposition and coating may vary according to the material that is used to form the EML.

The EML may be formed of any material that is commonly used to form EMLs, without limitation. The EML may be formed of any known host and dopant, and the dopant may be any known fluorescent or phosphorescent dopant.

Nonlimiting examples of suitable host materials include $Alq_3$, 4,4'-N,N'-dicarbazole-biphenyl (CBP), poly(n-vinylcarbazole) (PVK), or distyrylarylene (DSA).

Nonlimiting examples of suitable dopants include $Ir(PPy)_3$ (PPy=phenylpyridine)(green), $(4,6-F2ppy)_2Irpic$, platinum (II) octaethylporphyrin (PtOEP), compounds represented by Formula 4, Firpric, TBPe, and the like.

Formula 4

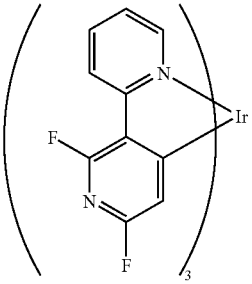

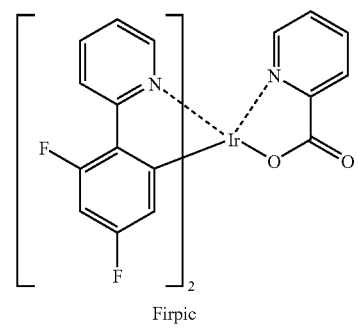

Firpic

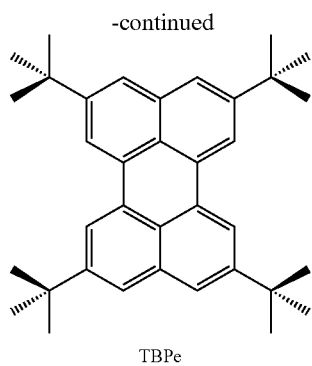

TBPe

The amount of the dopant may range from about 0.1 to about 20 parts by weight based on 100 parts by weight of the material that is used to form the EML (i.e., the total weight of the host and dopant). In one embodiment, for example, the amount of the dopant ranges from about 0.5 to about 12 parts by weight based on 100 parts by weight of the material that is used to form the EML (i.e., the total weight of the host and dopant). If the amount of the dopant is less than about 0.1 parts by weight, the effects of the dopant are negligible. On the other hand, if the amount of the dopant is greater than about 20 parts by weight, concentration quenching may occur.

The thickness of the EML may range from about 100 Å to about 1000 Å. In one embodiment, for example, the thickness ranges from about 200 Å to about 600 Å. When the thickness of the EML is less than about 100 Å, the emitting ability of the EML may decrease. On the other hand, when the thickness of the EML is greater than about 1000 Å, the driving voltage of the OLED may increase.

A HBL (as shown in FIG. 1) may be formed on the EML in order to prevent diffusion of triplet excitons or holes into the ETL when a phosphorescent dopant is used to form the EML. The HBL may be formed of any material that is commonly used to form HBLs, without limitation. Nonlimiting examples of suitable materials for the HBL include oxadiazole derivatives, triazole derivatives, phenanthroline derivatives, BAlq, and BCP.

The thickness of the HBL may range from about 50 Å to about 1000 Å. In one embodiment, for example, the thickness ranges from about 100 Å to about 300 Å. When the thickness of the HBL is less than about 50 Å, the hole blocking ability of the HBL may decrease. On the other hand, when the thickness of the HBL is greater than about 1000 Å, the driving voltage of the OLED may increase.

An ETL is formed on the HBL or EML by vacuum deposition, spin coating, casting, or the like. When the ETL is formed by vacuum deposition or spin coating, the conditions for deposition and coating are, in general, similar to those described above with respect to the formation of the HIL, although the conditions for deposition and coating may vary according to the material that is used to form the ETL.

The ETL may be formed of a bipyridine-based compound represented by Formula 1 described above. The ETL may also include a quinoline derivative, nonlimiting examples of which include tris(8-quinolinorate)aluminum ($Alq_3$), TAZ, and the like.

The thickness of the ETL may range from about 100 Å to about 1000 Å. In one embodiment, for example, the thickness may range from about 100 Å to about 500 Å. When the thickness of the ETL is less than about 100 Å, the electron transporting ability of the ETL may decrease. On the other hand, when the thickness of the ETL is greater than about 1000 Å, the driving voltage of the OLED may increase.

An EIL, which is formed of a material that allows easy injection of electrons from the cathode, can be formed on the ETL. Nonlimiting examples of suitable materials for the EIL include LiF, NaCl, CsF, $Li_2O$, BaO, and the like. The conditions for deposition of the EIL are, in general, similar to the conditions described above with respect to the formation of the HIL, although the conditions may vary according to the material that is used to form the EIL.

The thickness of the EIL may range from about 1 Å to about 100 Å. In one embodiment, for example, the thickness ranges from about 5 Å to about 90 Å. When the thickness of the EIL is less than about 1 Å, the electron injecting ability of the EIL may decrease. On the other hand, when the thickness of the EIL is greater than about 100 Å, the driving voltage of the OLED may increase.

Finally, a second electrode can be formed on the EIL by vacuum deposition, sputtering, or the like. The second electrode can be used as a cathode or an anode. The second electrode may be formed of a low work-function metal, an alloy, an electrically conductive compound, or a combination thereof. Nonlimiting examples of suitable materials for the second electrode include Li, Mg, Al, Al—Li, Ca, Mg—In, Mg—Ag, or the like. Alternatively, a transparent cathode formed of ITO or IZO can be used to produce a front surface light emitting device.

Hereinafter, the synthesis of some exemplary compounds and manufacture of OLEDs including organic layers having these compounds will be described. However, the Synthesis Examples and Examples are provided for illustrative purposes only, and are not intended to limit the scope of the present invention.

EXAMPLES

Synthesis Example 1

Synthesis of Compound 1

Compound 1 was synthesized through Reaction Scheme 1 below:

Reaction Scheme 1

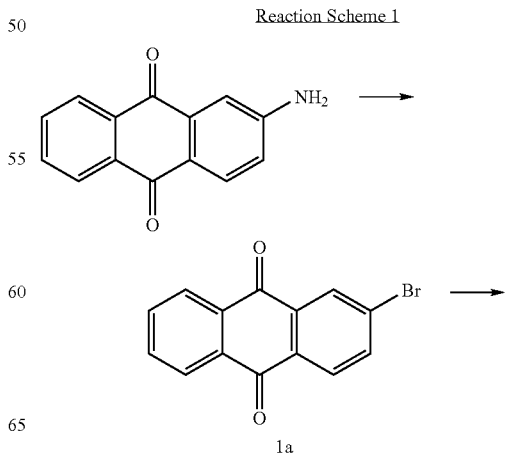

1a

27
-continued

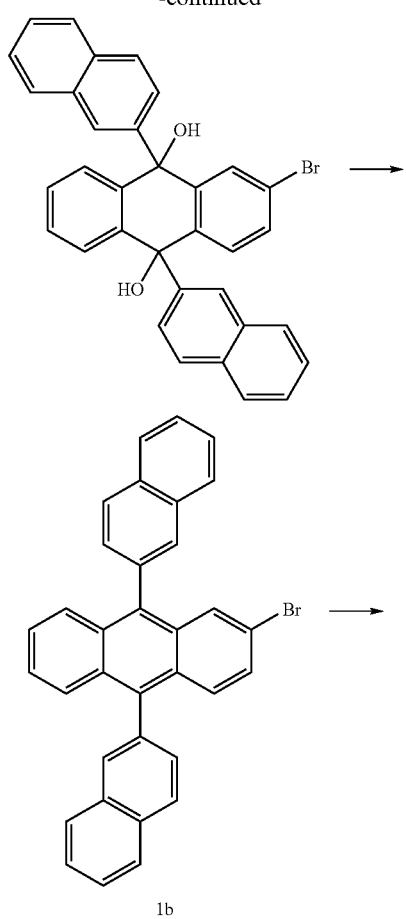

28
-continued

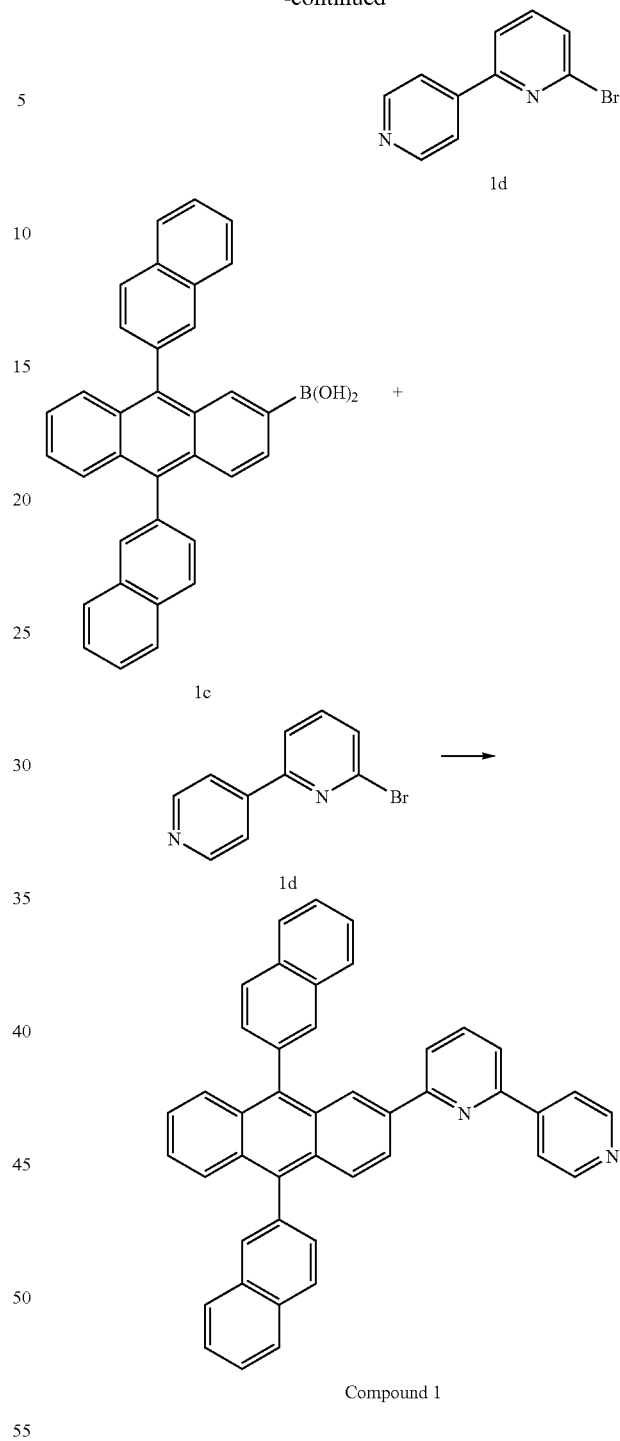

Compound 1

Synthesis of Intermediate 1a 10 g (44 mmol) of copper bromide and 8 g (35.8 mmol) of 2-aminoanthraquinone were added to 250 ml of bromic acid and the mixture was heated at 65° C. After gas generation was completed, the mixture was cooled to room temperature and added to 1000 ml of a 20% HCl solution. The resulting product was subject to extraction using dichloromethane. Residual moisture was removed using anhydrous magnesium sulfate and the resulting product was dried under reduced pressure. The dried resulting product was separated using

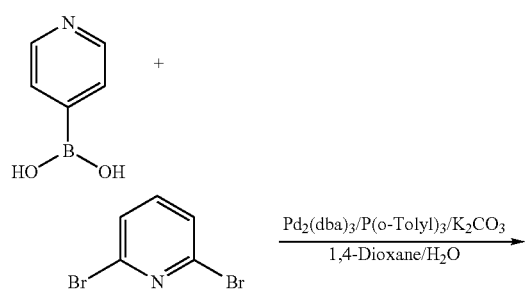

column chromatography (dichloromethane:n-hexane=4:1) to obtain 7.7 g of Intermediate 1a.

Synthesis of Intermediate 1b 10 g (34.8 mmol) of Intermediate 1a was added to 100 ml dried tetrahydrofuran (THF) under a nitrogen atmosphere, and the mixture was cooled to −78° C. Then, 10 mmol of 0.5M 2-naphthyl magnesium bromide was gradually added thereto. The temperature of the mixture was raised to room temperature and the mixture was stirred for 3 hours. An ammonium chloride solution was added to the mixture and the resulting product was subject to extraction using methylene chloride. An organic layer was dried using anhydrous magnesium sulfate and the solvent was evaporated. After the resulting product was dissolved in a small amount of ethyl ether, petroleum ether was added thereto and the mixture was stirred for several hours to obtain a solid compound. The solid compound was filtered and dried in a vacuum to obtain 17.6 g of dinaphthyldialcohol.

17.6 g (32.4 mmol) of the dinaphthyldialcohol was dispersed in 200 ml of acetic acid under a nitrogen atmosphere, and 53.4 g (330 mmol) of potassium iodide and 58 g (660 mmol) of sodium hypophosphite hydrate were added thereto. Then, the mixture was stirred and refluxed for 3 hours. Then, the mixture was cooled to room temperature, washed with water and methanol, and dried in a vacuum to obtain 11.3 g of light yellow Intermediate 1b.

Synthesis of Intermediate 1c 5 g (9.81 mmol) of Intermediate 1b was dissolved in 70 ml of dried THF under a nitrogen atmosphere and 4.7 ml (11.8 mmol) of butyl lithium was added thereto at −78° C. The resulting product was stirred at the same temperature for 1 hour, and 2.20 ml (29.4 mmol) of trimethyl borate was added thereto. The temperature of the mixture was raised to room temperature, a 2N HCl solution was added thereto after 1 hour, and the mixture was stirred for 3 hours. The resulting solid compound was filtered while washing with toluene to obtain 3.27 g of yellow Intermediate 1c (Yield: 70%).

Synthesis of Intermediate 1d 181.16 g (764.72 mmol) of 2,6-dibromo pyridine and 132 g (955.9 mmol) of $K_2CO_3$ were dissolved in a mixed solution of 1,4-dioxane and $H_2O$ (v/v=1000 mL:500 mL). 47 g (382.36 mmol) of pyridine-4-boronic acid, 7 g (7.65 mmol) of tris(dibenzylideneacetone)di-palladium and $P(o\text{-Tolyl})_3$ were added thereto and the mixture was refluxed for 12 hours while heating at 105° C. After the reaction was completed, the mixture was cooled to room temperature and washed with ethyl acetate while being filtered with Cellite. The resulting product was subject to extraction twice using ethyl acetate by adding a NaCl solution to a water layer. The resulting product was dried using $MgSO_4$, concentrated, filtered using column chromatography (Hex:EA=1:1), and suspension-stirred in a Hexane(30 mL)-Ether(10 mL) solution, and then filtered to obtain 22.5 g of Intermediate 1d (Yield: 25%). $^1$H NMR (300 MHz, $CDCl_3$) δ 7.52 (d, 1H), 7.66 (t, 1H), 7.76 (d, 1H) 7.87 (d, 2H), 8.73 (d, 2H).

Synthesis of Compound 1

6.0 g (12.63 mmol) of Intermediate 1c and 2.7 g (11.48 mmol) of Intermediate 1d were added to a mixed solvent of 4.76 g (34.4 mmol) potassium carbonate solution and THF, 398 mg (3 mol %) of $Pd(PPh_3)_4$ was added thereto while stirring, and the mixture was heated for 12 hours. The mixture was cooled to room temperature and subject to extraction using dichloromethane. Then, an organic layer was collected, and the solvent was removed by drying the organic layer using anhydrous magnesium sulfate under reduced pressure. The resulting product was filtered using column chromatography (ethyl acetate:dichloromethane=3:7) to obtain 5.3 g of yellow solid Compound 1 (Yield: 80%). $^1$H NMR (500 MHz, $CDCl_3$) δ 8.73 (d, 1H), 8.49 (d, 1H), 8.18-8.10 (m, 5H), 8.05 (dd, 2H), 8.01 (d, 1H), 7.97 (d, 1H), 7.88 (d, 1H), 7.84 (m, 1H), 7.80-7.62 (m, 13H), and 7.36 (dd, 2H).

Synthesis Example 2

Synthesis of Compound 6

Yellow solid Compound 6 was synthesized as in Synthesis Example 1 except that pyrene-1-boronic acid was used instead of Intermediate 1c (Yield: 83%). $^1$H NMR (500 MHz, $CDCl_3$) δ 8.75 (dd, 2H), 8.50 (d, 1H), 8.29 (d, 1H), 8.26-8.20 (m, 3H), 8.14-7.99 (m, 7H), 7.90 (dd, 1H), and 7.80 (dd, 1H).

Synthesis Example 3

Synthesis of Compound 7

Compound 7 was synthesized according to Reaction Scheme 2 below:

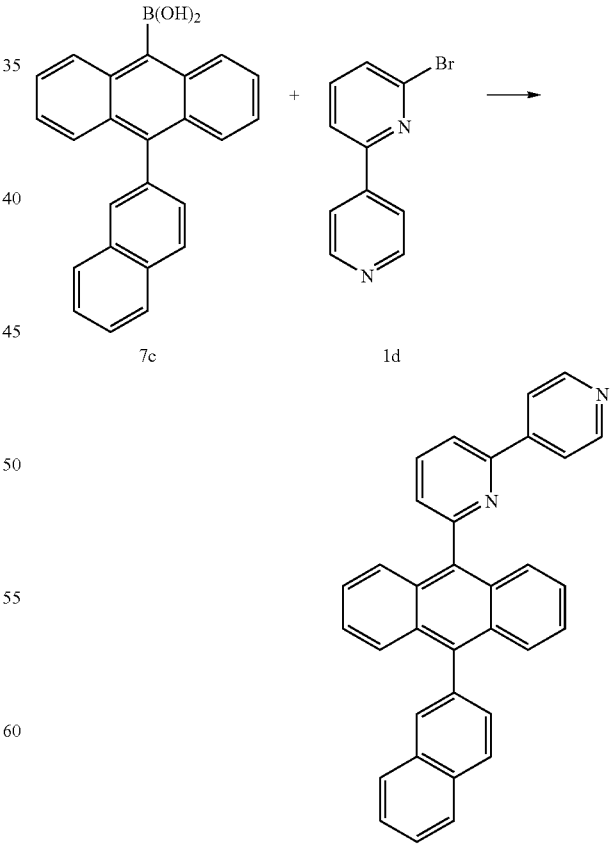

As shown in Reaction Scheme 2, yellow powder Compound 7 was synthesized as in Synthesis Example 1 except that Intermediate 7c was used instead of Intermediate 1c. $^1$H NMR (500 MHz, CDCl$_3$) δ 8.68 (dd, 2H), 8.13-7.94 (m, 8H), 7.74-7.60 (m, 8H), and 7.37-7.33 (m, 4H).

Synthesis Example 4

Synthesis of Compound 8

Compound 8 was synthesized according to Reaction Scheme 3 below:

Reaction Scheme 3

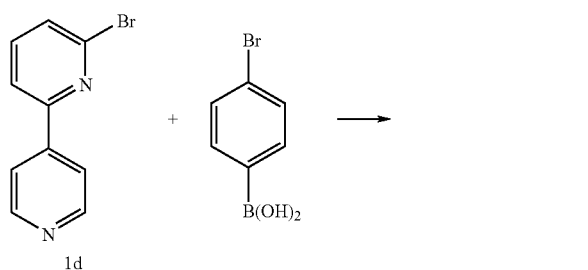

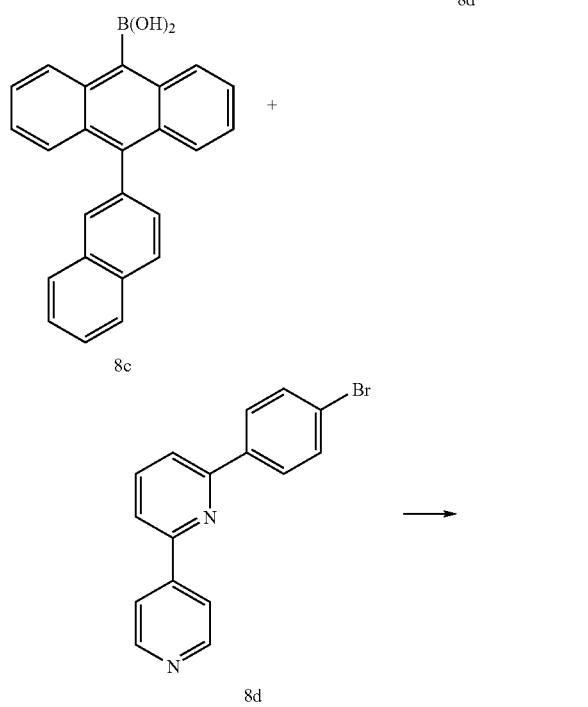

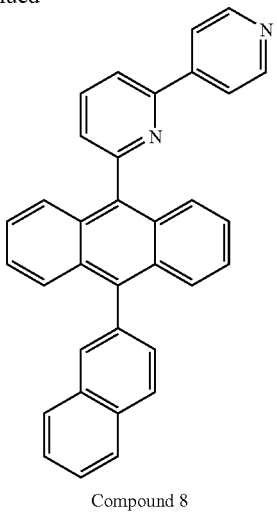

Compound 8

Intermediate 8d was synthesized by reacting Compound 1d with 4-bromophenylboronic acid through a Suzuki coupling reaction. 6.27 g (18 mmol) of Intermediate 8c and 4.67 g (15 mmol) of Intermediate 8d were added to a mixed solvent of THF and K$_2$CO$_3$ solution, 0.52 g (3 mol %) of Pd(PPh$_3$)$_4$ was added thereto while stirring, and the mixture was heated for 12 hours. The mixture was cooled to room temperature and subject to extraction using dichloromethane. Then, an organic layer was collected, and the solvent was removed by drying the organic layer using anhydrous magnesium sulfate under reduced pressure. The resulting product was filtered using column chromatography (ethyl acetate:dichloromethane=3:7) to obtain 6.8 g of yellow solid Compound 8 (Yield: 85%). $^1$H NMR (500 MHz, CDCl$_3$) δ 8.79 (dd, 2H), 8.41 (d, 2H), 8.12-8.08 (m, 3H), 8.06-7.93 (m, 5H), 7.87-7.79 (m, 3H), 7.74 (dd, 2H), 7.69-7.60 (m, 5H), 7.38-7.31 (m, 4H).

Synthesis Example 5

Synthesis of Compound 11

Compound 11 was synthesized according to Reaction Scheme 4 below:

Reaction Scheme 4

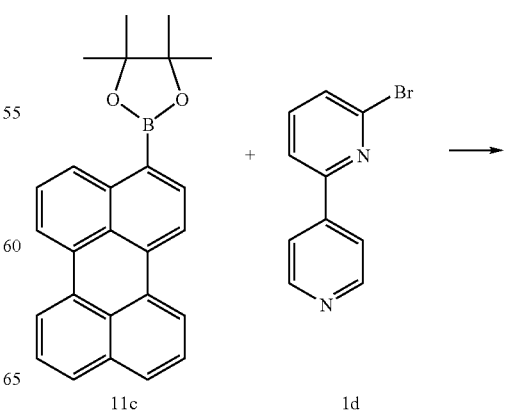

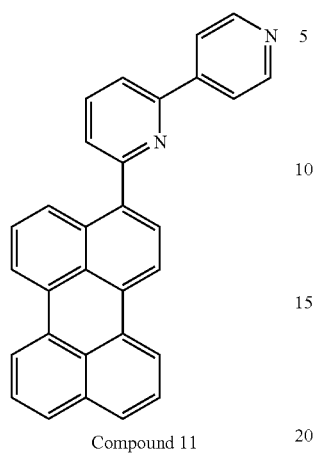

Compound 11

As shown in Reaction Scheme 4, yellow solid Compound 11 was synthesized as in Synthesis Example 1 except that Intermediate 11c was used instead of Intermediate 1c (Yield: 82%). $^1$H NMR (500 MHz, CDCl$_3$) δ 8.73 (dd, 2H), 8.32 (d, 1H), 8.25 (t, 3H), 8.08 (d, 1H), 8.03 (dd, 2H), 7.98 (t, 1H), 7.87 (d, 1H), 7.74-7.67 (m, 4H), 7.53-7.50 (m, 3H).

Synthesis Example 6

Synthesis of Compound 13

Compound 13 was synthesized according to Reaction Scheme 5 below:

Reaction Scheme 5

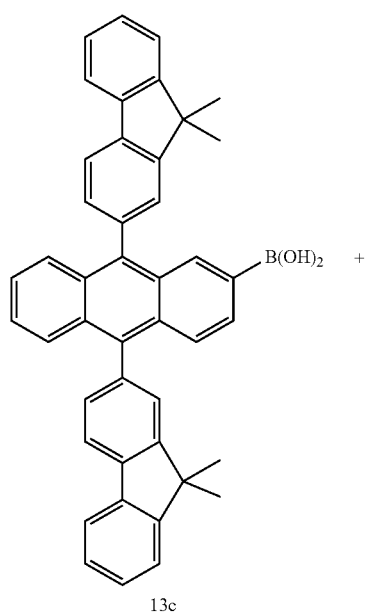

13c

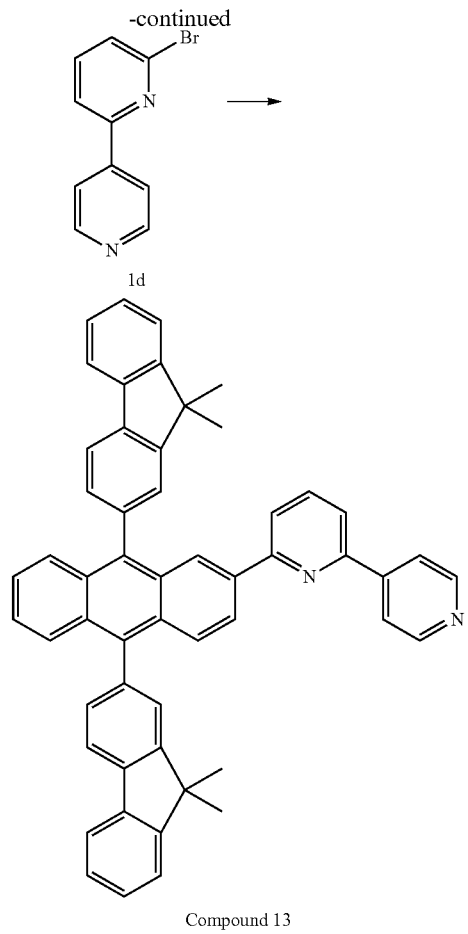

Compound 13

As shown in Reaction Scheme 5, yellow solid Compound 13 was synthesized as in Synthesis Example 1 except that Intermediate 13c was used instead of Intermediate 1c (Yield: 74%). $^1$H NMR (500 MHz, CDCl$_3$) δ 8.69 (1 H), 8.41 (dd, 2H), 8.18 (dd, 1H), 8.02 (dd, 2H), 7.96-7.38 (m, 22H), 1.60 (s, 6H), 1.58 (s, 6H).

Synthesis Example 7

Synthesis of Compound 15

Compound 15 was synthesized according to Reaction Scheme 6 below:

Reaction Scheme 6

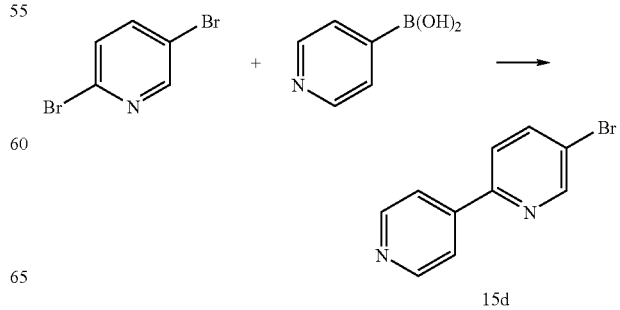

15d

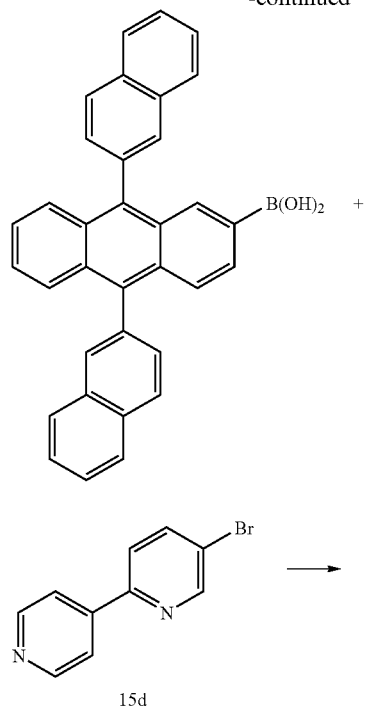

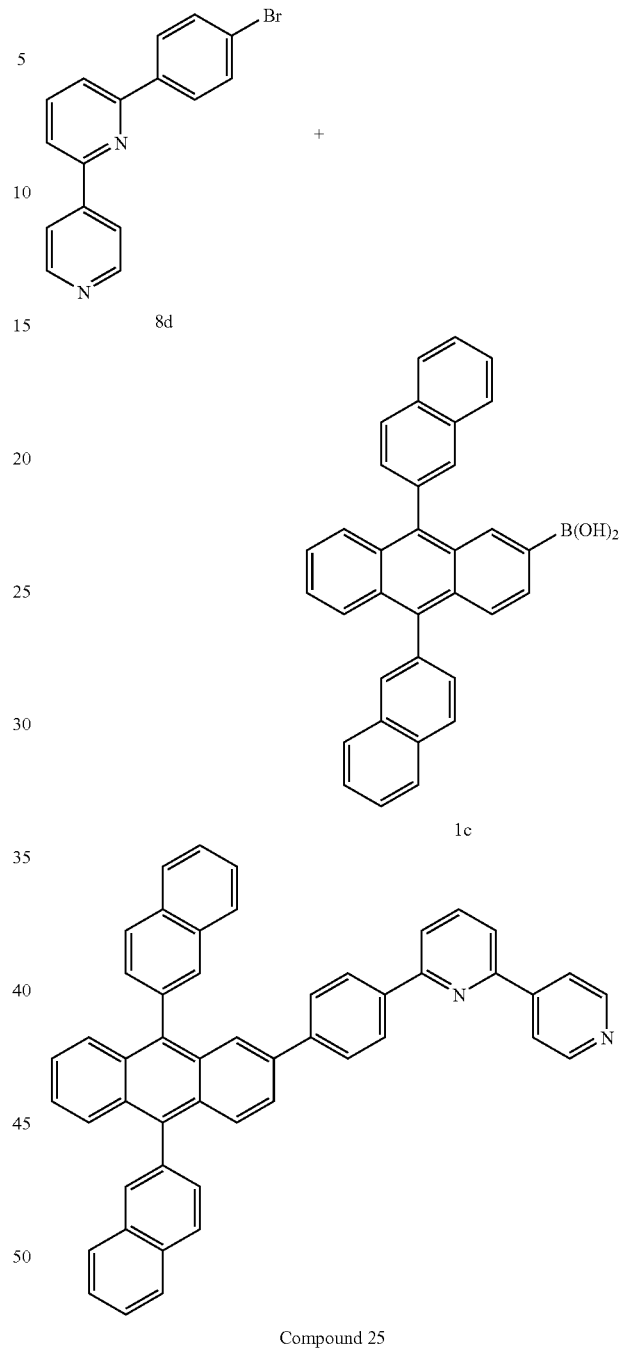

As shown in Reaction Scheme 6, Compound 15d was synthesized as in Synthesis Example 1 except that 2,5-dibromo pyridine was used instead of 2,6-dibromo pyridine in the synthesis of Intermediate 1d. Then, yellow powder Compound 15 was synthesized through a Suzuki coupling reaction, as shown in Reaction Scheme 6. $^1$H NMR (500 MHz, CDCl$_3$) 8.87 (d, 1H), 8.64 (d, 2H), 8.13 (d, 2H), 8.07-8.04 (m, 5H), 7.98-7.62 (m 16H), and 7.36-7.33 (m, 2H).

Synthesis Example 8

Synthesis of Compound 25

Compound 25 was synthesized according to reaction scheme 7 below:

As shown in Reaction Scheme 7, Compound 25 was synthesized as in Synthesis Example 1, except that Intermediate 8d was used instead of Intermediate 1d. $^1$H NMR (500 MHz, CDCl$_3$) δ 8.69 (2H), 8.15-7.63 (m, 28H), and 7.34-7.32 (m, 2H)

Synthesis Example 9

Synthesis of Compound 27

Compound 27 was synthesized according to Reaction Scheme 8 below:

Reaction Scheme 8

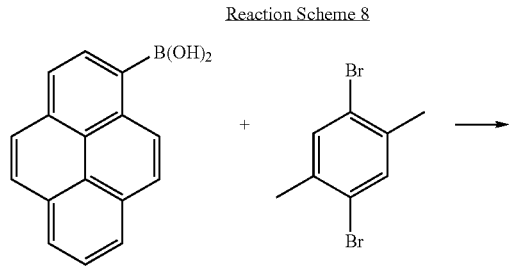

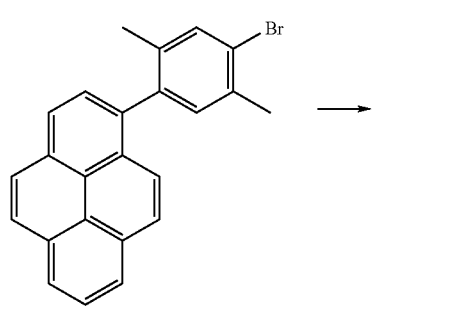

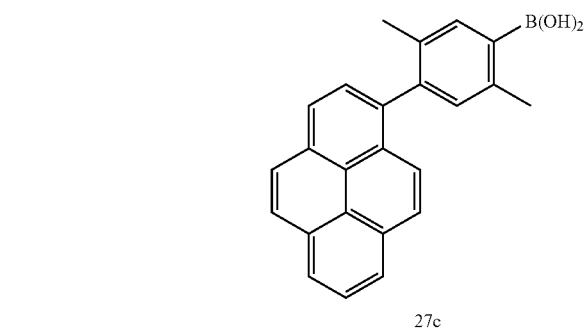

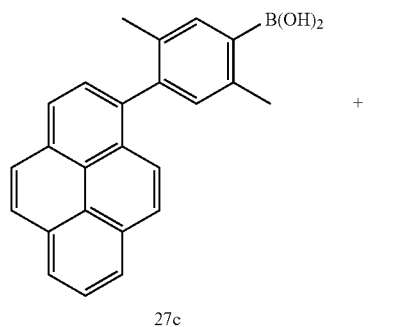

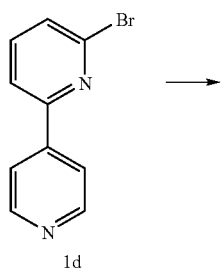

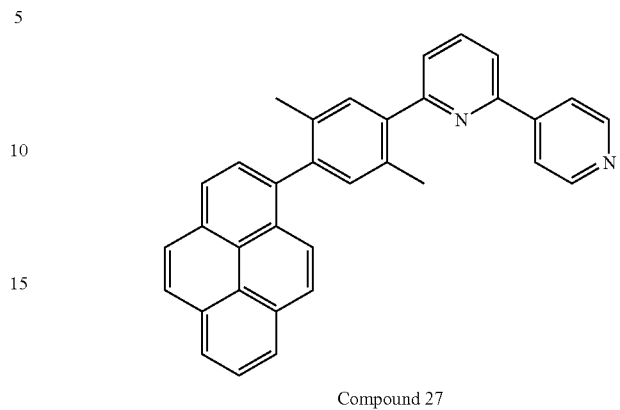

Compound 27

4.92 g (20 mmol) of pyrene-1-boronic acid and 10.6 g (40 mmol) of 2,5-dibromo-p-xylene were dissolved in a mixed solution of THF and 8.3 g (60 mmol) of $K_2CO_3$. 0.7 g of (0.6 mmol) of tetrakis(triphenylphospine)palladium was added thereto, and the mixture was refluxed while heating for 12 hours. The resulting product was subject to extraction using ethyl acetate, separated using column chromatography (developing solvent:Hex) and dried (6.1 g, Yield: 80%). The product was dissolved in dried THF under a nitrogen atmosphere and cooled to −78° C. Then, 7.6 ml of n-butyl lithium (2.5M solution in Hexane) was gradually added thereto. After the resulting product was maintained at −78° C. for 1 hour, 2.6 ml (23.7 mmol) of trimethylborate was added thereto and the mixture was heated to room temperature. A 2N HCl solution was added thereto and subject to extraction using ethyl acetate. The resulting product was recrystallized using methylene chloride (in Hexane) to obtain 3.9 g of white solid Compound 27c (Yield: 70%).

Compound 27c was reacted with Intermediate 1d by a Suzuki coupling reaction as described above to obtain 4.2 g yellow powder Compound 27 (Yield: 82%). $^1$H NMR (300 MHz, $CDCl_3$) Δ 8.73 (dd, 2H), 8.29-8.12 (m, 3H), 8.14 (d, 2H), 8.05-8.01 (m, 4H), 7.98-7.93 (m, 2H), 7.87-7.83 (m, 2H), 7.63 (d, 1H), 7.53 (s, 1H), 7.34 (s, 1H), 2.51 (s, 3H), and 2.08 (s, 1H).

Comparative Synthesis Example A

Comparative Compound A was synthesized as in Synthesis Example 1, except that Intermediate 1c was reacted with 2-bromo pyridine instead of being reacted with Intermediate 1d. $^1$H NMR (300 MHz, $CDCl_3$) δ 8.56 (d, 1H), 6.98 (dd, 1H), 8.12-7.89 (m, 7H), 7.73-7.47 (m, 10H), and 7.39-7.32 (m, 6H).

Compound A

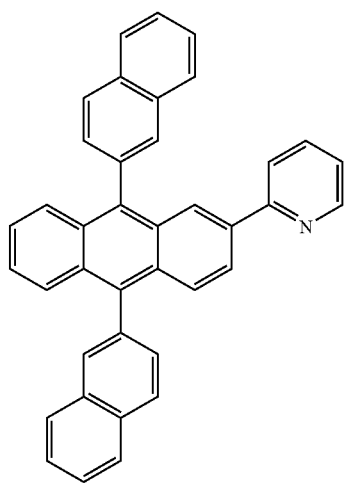

Compound C

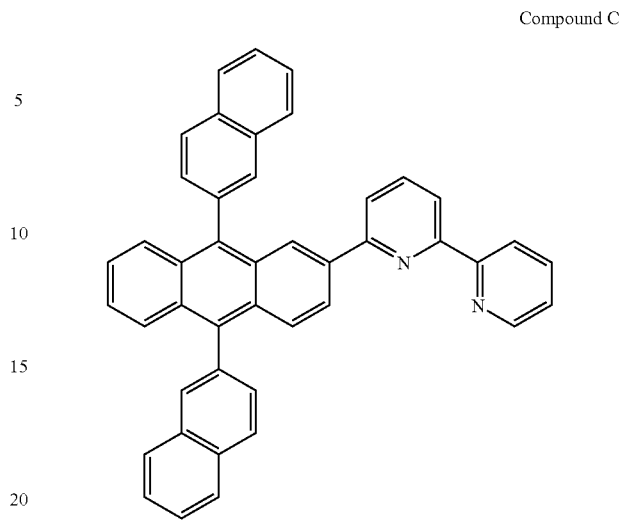

Comparative Synthesis Example B

Comparative Compound B was synthesized as in Synthesis Example 1, except that pyridine-3-boronic acid was used instead of pyridine-4-boronic acid in the synthesis of Intermediate 1d. $^1$H NMR (300 MHz, CDCl$_3$) δ 9.21 (1H), 8.61-7.98 (6H), 7.91-7.67 (10H), 7.56-7.38 (7H), and 7.32-7.18 (4H).

Comparative Synthesis Example D

Comparative Compound D was synthesized as in Synthesis Example 3, except that 2,5-dibromo pyridine was used instead of 2,6-dibromo pyridine, and tributyl(2-pyridyl)tin was used instead of pyridie-4-boronic acid in the synthesis of Intermediate 1d. $^1$H NMR (300 MHz, CDCl$_3$) δ 9.15 (d, 1H), 8.86 (d, 1H), 8.58-8.49 (m, 2H), 8.13-7.71 (m, 9H), 7.76-7.49 (m, 9H), and 7.39-7.31 (m, 6H).

Compound B

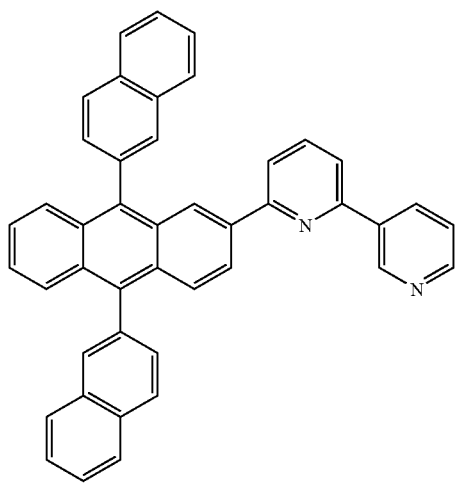

Compound D

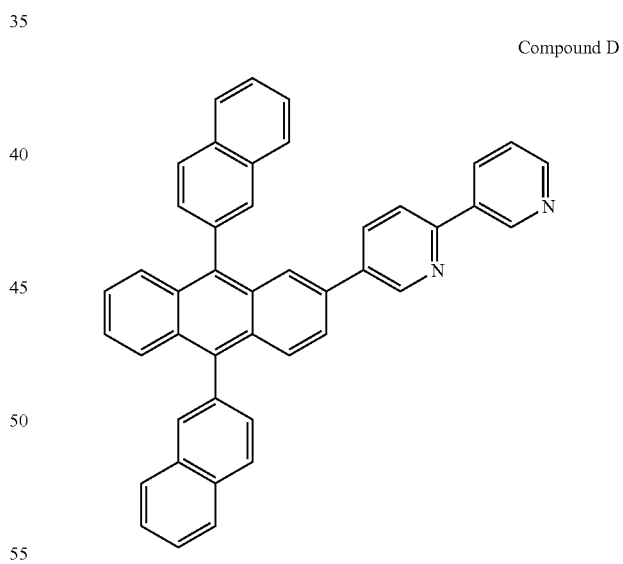

Comparative Synthesis Example C

Comparative Compound C was synthesized as in Synthesis Example 1, except that tributyl(2-pyridyl)tin was used instead of pyridine-4-boronic acid in the synthesis of Intermediate 1d. $^1$H NMR (300 MHz, CDCl$_3$) δ 8.72 (d, 1H), 8.62 (m, 1H), 8.27 (dd, 1H), 8.17-7.97 (m, 10H), 7.89 (d, 1H), 7.85-7.62 (m, 10H), 7.47-7.21 (m, 4H).

Comparative Synthesis Example E

Comparative Compound E was synthesized as in Synthesis Example 3, except that 2,5-dibromo pyridine was used instead of 2,6-dibromo pyridine, and tributyl(2-pyridyl)tin was used instead of pyridine-4-boronic acid in the synthesis of Intermediate 1d. $^1$H NMR (300 MHz, CDCl$_3$) δ 8.82 (d, 1H), 8.65 (d, 1H), 8.39-8.33 (m, 2H), 8.17-7.94 (m, 10H), 7.90 (d, 1H), 7.79-7.62 (m, 11H), and 7.36-7.33 (m, 2H).

Compound E

Example 1

A 15Ω/cm² (1200 Å) ITO glass substrate (obtained from Corning Co.) was cut to a size of 50 mm×50 mm×0.7 mm, microwave washed with isopropyl alcohol for 5 minutes, microwave washed with pure water for 5 minutes, and washed with UV ozone for 30 minutes. m-MTDATA was vacuum deposited on the substrate to form a HIL with a thickness of 750 Å. α-NPD was vacuum deposited on the HIL to form a HTL with a thickness of 150 Å. 97 wt % of DSA as a host and 3 wt % of TBPe as a dopant were deposited on the HTL to form an EML with a thickness of 300 Å. Compound 1, prepared according to Synthesis Example 1, was vacuum deposited on the EML to form an ETL with a thickness of 200 Å. LiF was vacuum deposited on the ETL to form an EIL with a thickness of 80 Å, and Al was vacuum deposited on the EIL to form a cathode with a thickness of 3000 Å.

Example 2

An OLED was manufactured as in Example 1, except that Compound 6, prepared according to Synthesis Example 2, was used instead of Compound 1 as the material of the ETL.

Example 3

An OLED was manufactured as in Example 1, except that Compound 7, prepared according to Synthesis Example 3, was used instead of Compound 1 as the material of the ETL.

Example 4

An OLED was manufactured as in Example 1, except that Compound 8, prepared according to Synthesis Example 4, was used instead of Compound 1 as the material of the ETL.

Example 5

An OLED was manufactured as in Example 1, except that Compound 11, prepared according to Synthesis Example 5, was used instead of Compound 1 as the material of the ETL.

Example 6

An OLED was manufactured as in Example 1, except that Compound 13, prepared according to Synthesis Example 6, was used instead of Compound 1 as the material of the ETL.

Example 7

An OLED was manufactured as in Example 1, except that Compound 15, prepared according to Synthesis Example 7, was used instead of Compound 1 as the material of the ETL.

Example 8

An OLED was manufactured as in Example 1, except that Compound 25, prepared according to Synthesis Example 8, was used instead of Compound 1 as the material of the ETL.

Example 9

An OLED was manufactured as in Example 1, except that Compound 27, prepared according to Synthesis Example 9, was used instead of Compound 1 as the material of the ETL.

Comparative Example 1

An OLED was manufactured as in Example 1, except that Compound A, prepared according to Comparative Synthesis Example A, was used instead of Compound 1 as the material of the ETL.

Comparative Example 2

An OLED was manufactured as in Example 1, except that Compound B, prepared according to Comparative Synthesis Example B, was used instead of Compound 1 as the material of the ETL.

Comparative Example 3

An OLED was manufactured as in Example 1, except that Compound C, prepared according to Comparative Synthesis Example C, was used instead of Compound 1 as the material of the ETL.

Comparative Example 4

An OLED was manufactured as in Example 1, except that Compound D, prepared according to Comparative Synthesis Example D, was used instead of Compound 1 as the material of the ETL.

Comparative Example 5

An OLED was manufactured as in Example 1, except that Compound E, prepared according to Comparative Synthesis Example E, was used instead of Compound 1 as the material of the ETL.

Comparative Analysis

The driving voltage (V), current density (mA/cm²), and efficiency (lm/W) of the OLEDs manufactured according to Examples 1 to 9 and Comparative Examples A to E were measured using a PR650 (Spectroscan) source measurement unit (PhotoResearch Inc.), and the results are shown in Table 1 below. In addition, the half-life of a brightness of 2000 nit was measured, and the results are shown in Table 1 below.

TABLE 1

| ETL | Voltage (mV) | Current density (mA/cm²) | Brightness (cd/m²) | Efficiency (lm/W) |
|---|---|---|---|---|
| Example 1 | Compound 1 | 5673 | 100 | 7011 | 7.01 |
| Example 2 | Compound 6 | 5375 | 100 | 8405 | 8.41 |
| Example 3 | Compound 7 | 5703 | 100 | 7661 | 7.66 |
| Example 4 | Compound 8 | 5628 | 100 | 9779 | 9.78 |
| Example 5 | Compound 11 | 5155 | 100 | 8399 | 8.40 |
| Example 6 | Compound 13 | 5507 | 100 | 5454 | 5.45 |
| Example 7 | Compound 15 | 5375 | 100 | 8405 | 8.41 |
| Example 8 | Compound 25 | 5783 | 100 | 8870 | 8.87 |
| Example 9 | Compound 27 | 4996 | 100 | 6183 | 6.18 |
| Comparative Example 1 | Compound A | 7075 | 100 | 5880 | 5.88 |
| Comparative Example 2 | Compound B | 7113 | 100 | 5766 | 5.77 |
| Comparative Example 3 | Compound C | 6969 | 100 | 5517 | 5.52 |
| Comparative Example 4 | Compound D | 7392 | 100 | 5856 | 5.86 |
| Comparative Example 5 | Compound E | 6431 | 100 | 4200 | 4.20 |

Figure 2:
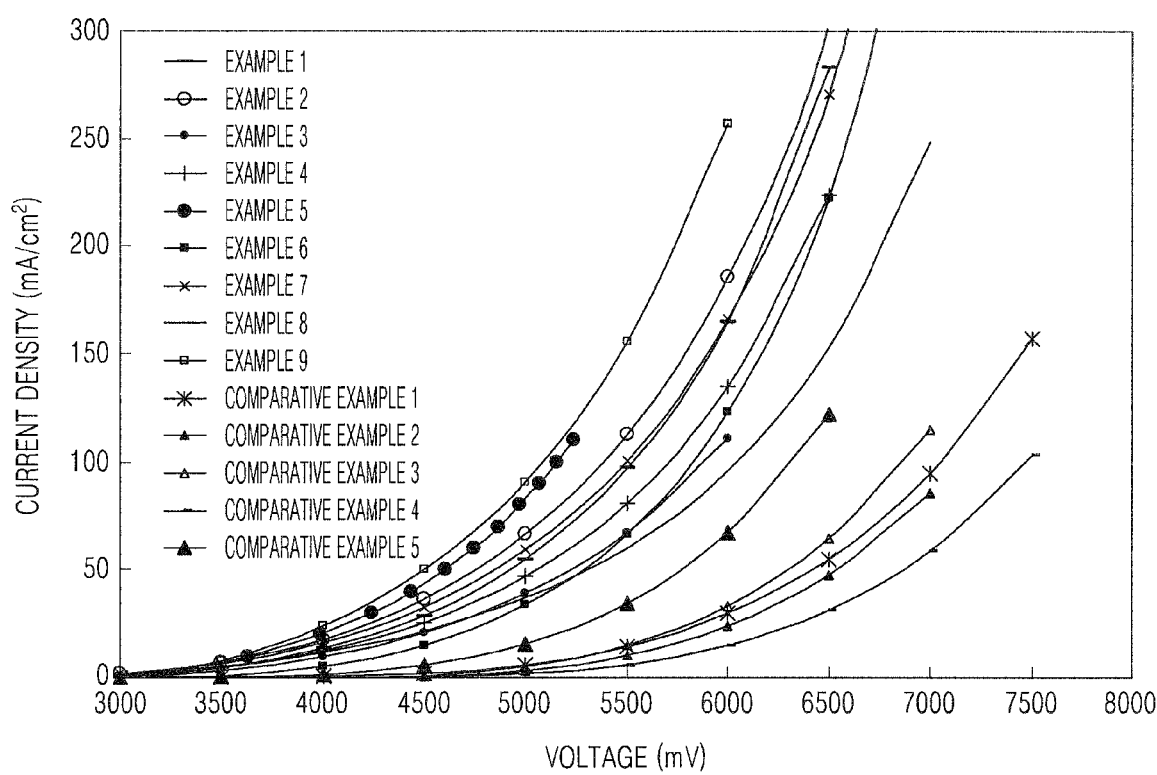
FIG. 2 is a graph comparing the voltage-current densities of the OLEDs prepared according to Examples 1 to 9 and Comparative Examples A to E.

FIG. 2 is a graph comparing the voltage-current densities of the OLEDs manufactured according to Examples 1 to 9 and Comparative Examples 1 to 5.

The OLEDs manufactured according to Examples 1 to 9 had improved driving voltage, current density, efficiency and lifetime characteristics as compared to the OLEDs manufactured according to Comparative Examples 1 to 5.

Since the bipyridine-based compounds represented by Formula 1 have good electron transporting capabilities, OLEDs including organic layers having the bipyridine-based compounds can have low driving voltages, high current densities, high efficiencies and long lifetimes. In particular, if N is at the para-position relative to the carbon of a second pyridine ring (not including an Ar or L substituent), and the carbon is bonded to a first pyridine ring (including an Ar or L substituent), the bipyridine-based compound can have unexpectedly good electron transporting capabilities making it suitable for use as an organic layer of an OLED.

While the present invention has been illustrated and described with reference to certain exemplary embodiments, those of ordinary skill in the art will recognize that various modifications and changes may be made to the described embodiments without departing from the spirit and scope of the present invention as defined by the following claims.

What is claimed is:

1. A bipyridine-based compound represented by Formula 1:

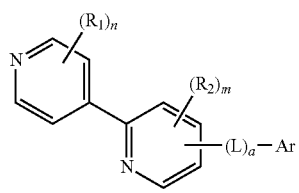

Formula 1 wherein:
each of $R_1$ and $R_2$ is independently selected from the group consisting of halogen atoms, hydroxyl groups, cyano groups, substituted and unsubstituted $C_1$-$C_{30}$ alkyl groups, substituted and unsubstituted $C_1$-$C_{30}$ alkoxy groups, substituted and unsubstituted $C_2$-$C_{30}$ alkenyl groups, substituted and unsubstituted $C_6$-$C_{30}$ aryl groups, and substituted and unsubstituted $C_3$-$C_{30}$ heteroaryl groups;

n is an integer of 0-4;

m is an integer of 0-3;

L is selected from the group consisting of substituted and unsubstituted $C_6$-$C_{30}$ arylene groups, and substituted and unsubstituted $C_3$-$C_{30}$ heteroarylene groups;

a is an integer of 0-5; and

Ar is selected from the group consisting of:
unsubstituted groups selected from the group consisting of anthracenyl groups, pyrenyl groups, chrysenyl groups, and perylenyl groups, and
substituted groups selected from the group consisting of anthracenyl groups, pyrenyl groups, chrysenyl groups, and perylenyl groups,
wherein the substituted groups are substituted with at least one substituent selected from the group consisting of halogen atoms, hydroxyl groups, nitro groups, cyano groups, amino groups, amidino groups, hydrazine groups, hydrazone groups, carboxyl groups and salts thereof, sulfone groups and salts thereof, phosphoric acid groups and salts thereof, $C_1$-$C_{30}$ alkoxy groups, $C_6$-$C_{30}$ aryl groups, pyrazolyl groups, imidazolyl groups, oxazolyl groups, thiazolyl groups, triazolyl groups, tetrazolyl groups, oxadiazolyl groups, pyridinyl groups, pyradizinyl groups, pyrimidinyl groups, carbazolyl groups, indolyl groups, quinolinyl groups, and isoquinolinyl groups.

2. The bipyridine-based compound of claim 1, wherein each of $R_1$ and $R_2$ is independently selected from the group consisting of halogen atoms, hydroxyl groups, cyano groups, substituted and unsubstituted $C_1$-$C_{10}$ alkyl groups, substituted and unsubstituted $C_2$-$C_{10}$ alkoxy groups, substituted and unsubstituted $C_6$-$C_{12}$ aryl groups, and substituted and unsubstituted $C_3$-$C_{12}$ heteroaryl groups.

3. The bipyridine-based compound of claim 1, wherein each of $R_1$ and $R_2$ is independently selected from the group consisting of halogen atoms, hydroxyl groups, cyano groups, $C_1$-$C_{10}$ alkyl groups, $C_1$-$C_{10}$ haloalkyl groups, phenyl groups, halophenyl groups, $C_1$-$C_{10}$ alkylphenyl groups, $C_1$-$C_{10}$ alkoxyphenyl groups, naphthyl groups, halonaphthyl groups, $C_1$-$C_{10}$ alkylnaphthyl groups, and $C_1$-$C_{10}$ alkoxynaphthyl groups.

4. The bipyridine-based compound of claim 1, wherein n is 0.

5. The bipyridine-based compound of claim 1, wherein m is 0.

6. The bipyridine-based compound of claim 1, wherein Ar is selected from the group consisting of substituted and unsubstituted anthracenyl groups.

7. The bipyridine-based compound of claim 1, wherein Ar is selected from the group consisting of compounds represented by Formula 4:

Formula 4
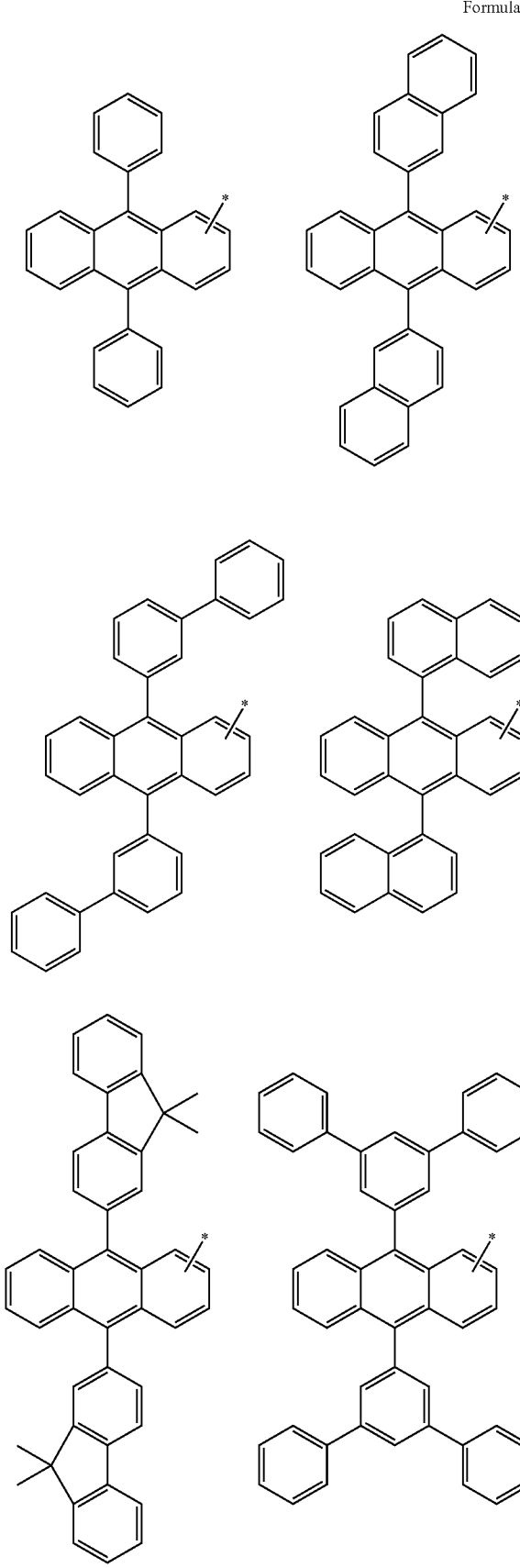
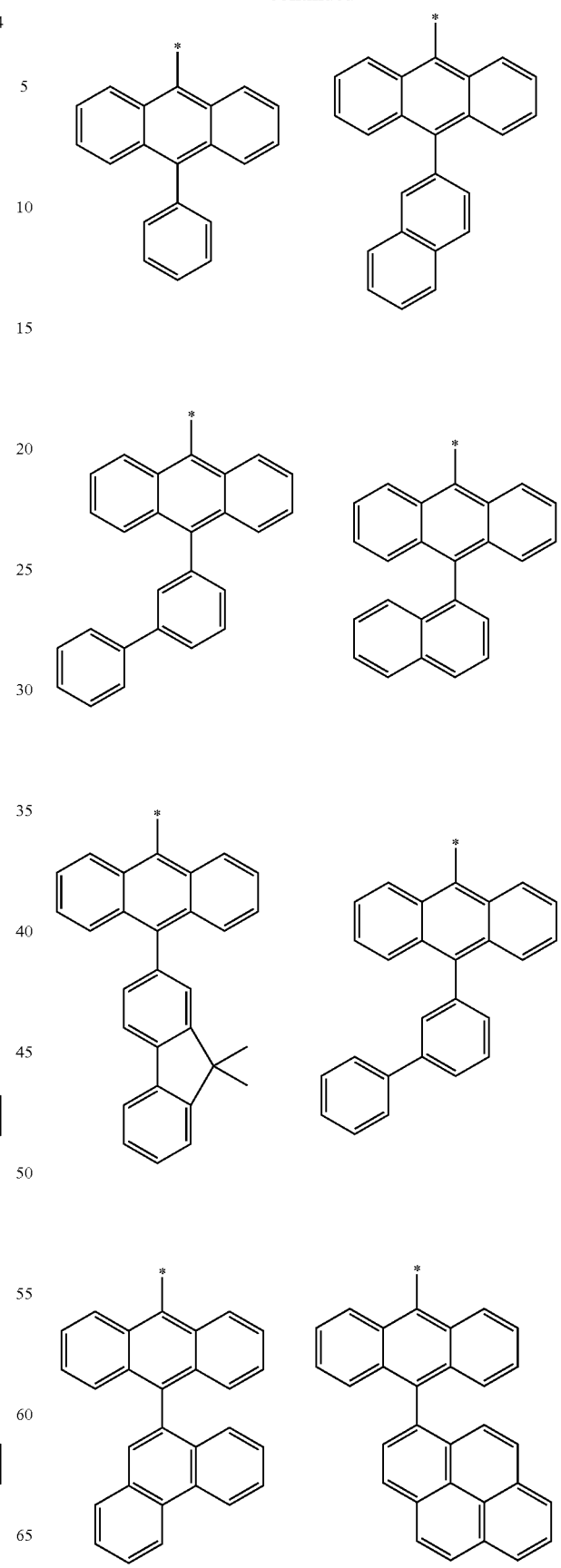

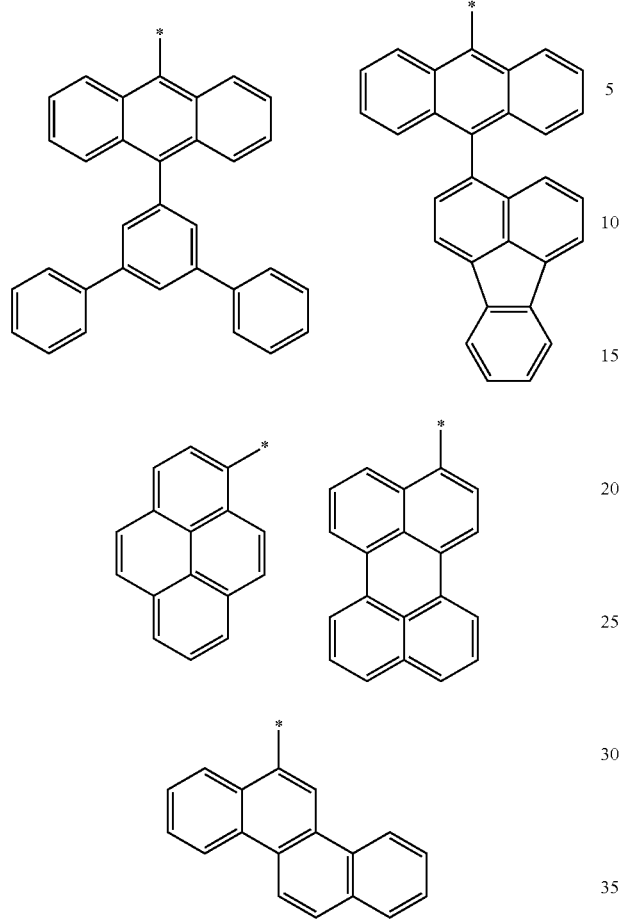
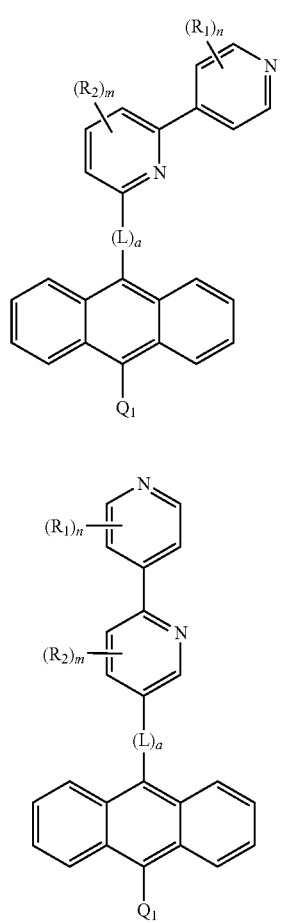
wherein * is a binding site with -(L)$_a$- or a bipyridyl group.
8. The bipyridine-based compound of claim 1, wherein the bipyridine-based compound is selected from the group consisting of compounds represented by Formulae 2a to 2j:
Formula 2a
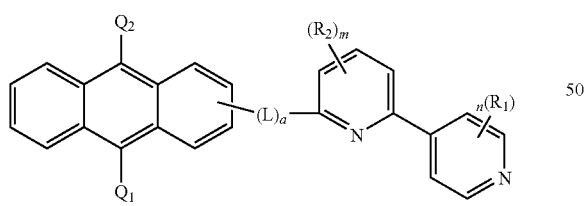
Formula 2b
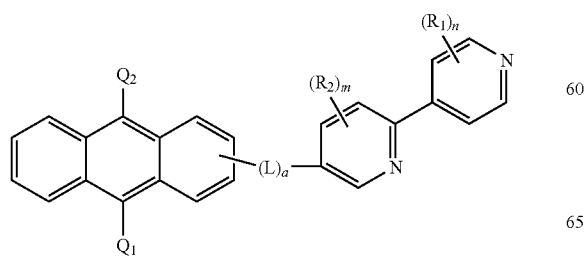
Formula 2c
Formula 2d
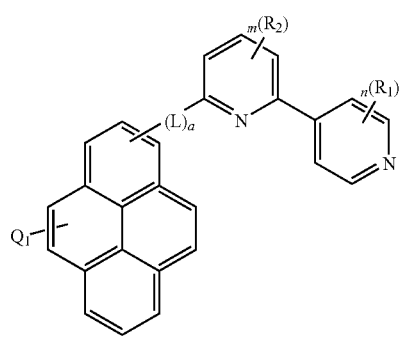
Formula 2e
Formula 2f
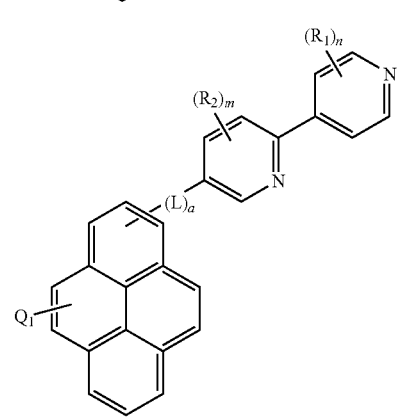

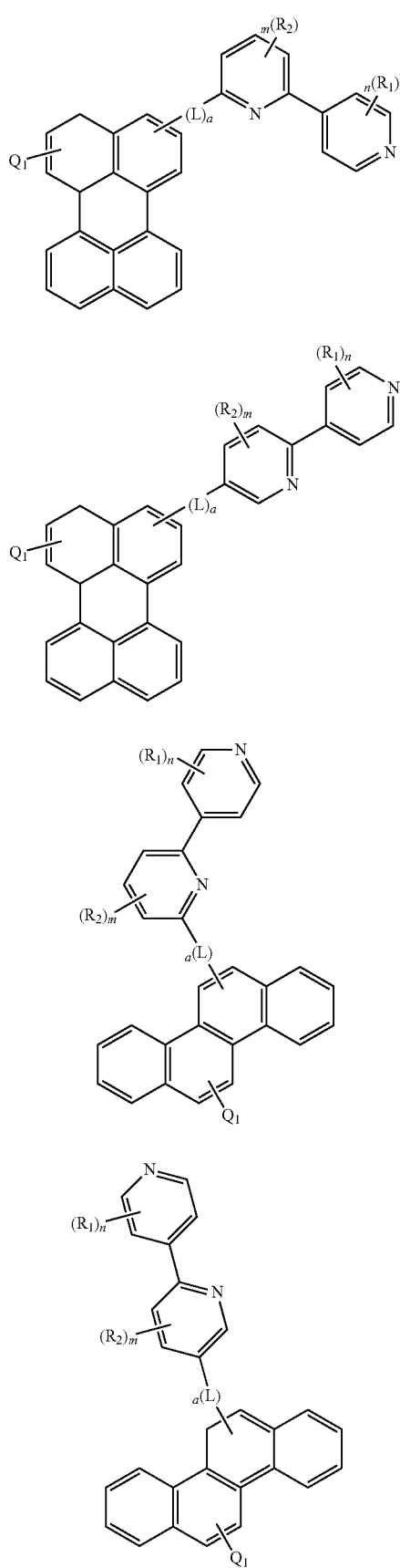

Formula 2g

Formula 2h

Formula 2i

Formula 2j wherein:
each of $R_1$ and $R_2$ is independently selected from the group consisting of halogen atoms, hydroxy groups, cyano groups, substituted and unsubstituted $C_1$-$C_{30}$ alkyl groups, substituted and unsubstituted $C_1$-$C_{30}$ alkoxy groups, substituted and unsubstituted $C_2$-$C_{30}$ alkenyl groups, substituted and unsubstituted $C_6$-$C_{30}$ aryl groups, and substituted and unsubstituted $C_3$-$C_{30}$ heteroaryl groups;
n is an integer ranging from 0 to 4;
m is an integer ranging from 0 to 3;
L is selected from the group consisting of substituted and unsubstituted $C_6$-$C_{30}$ arylene groups, and substituted and unsubstituted $C_3$-$C_{30}$ heteroarylene groups;
a is an integer ranging from 0 to 5; and
each of $Q_1$ and $Q_2$ is independently selected from the group consisting of halogen atoms, cyano groups, hydroxyl groups, $C_1$-$C_{10}$ alkyl groups, $C_1$-$C_{10}$ alkoxy groups, phenyl groups, phenyl groups substituted with at least one $C_1$-$C_{10}$ alkyl group or at least one $C_6$-$C_{12}$ aryl group, naphthyl groups, naphthyl groups substituted with at least one $C_1$-$C_{10}$ alkyl group or at least one $C_6$-$C_{12}$ aryl group, anthracenyl groups, anthracenyl groups substituted with at least one $C_1$-$C_{10}$ alkyl group or at least one $C_6$-$C_{12}$ aryl group, fluorenyl groups, fluorenyl groups substituted with at least one $C_1$-$C_{10}$ alkyl group or at least one $C_6$-$C_{12}$ aryl group, phenanthrenyl groups, phenanthrenyl groups substituted with at least one $C_1$-$C_{10}$ alkyl group or at least one $C_6$-$C_{12}$ aryl group, pyrenyl groups, pyrenyl groups substituted with at least one $C_1$-$C_{10}$ alkyl group or at least one $C_6$-$C_{12}$ aryl group, fluoranthrenyl groups, and fluoranthrenyl groups substituted with at least one $C_1$-$C_{10}$ alkyl group or at least one $C_6$-$C_{12}$ aryl group.

9. The bipyridine-based compound of claim 8, wherein each of $Q_1$ and $Q_2$ is independently selected from the group consisting of phenyl groups, phenyl groups substituted with at least one $C_1$-$C_{10}$ alkyl group or at least one $C_6$-$C_{12}$ aryl group, naphthyl groups, naphthyl groups substituted with at least one $C_1$-$C_{10}$ alkyl group or at least one $C_6$-$C_{12}$ aryl group, anthracenyl groups, anthracenyl groups substituted with at least one $C_1$-$C_{10}$ alkyl group or at least one $C_6$-$C_{12}$ aryl group, fluorenyl groups, fluorenyl groups substituted with at least one $C_1$-$C_{10}$ alkyl group or at least one $C_6$-$C_{12}$ aryl group, phenanthrenyl groups, phenanthrenyl groups substituted with at least one $C_1$-$C_{10}$ alkyl group or at least one $C_6$-$C_{12}$ aryl group, pyrenyl groups, pyrenyl groups substituted with at least one $C_1$-$C_{10}$ alkyl group or at least one $C_6$-$C_{12}$ aryl group, fluoranthrenyl groups, and fluoranthrenyl groups substituted with at least one $C_1$-$C_{10}$ alkyl group or at least one $C_6$-$C_{12}$ aryl group.

10. The bipyridine-based compound of claim 1, wherein the bipyridine-based compound is selected from the group consisting of compounds represented by Formulae 3a, 3b, and 3e to 3j:

Formula 3a

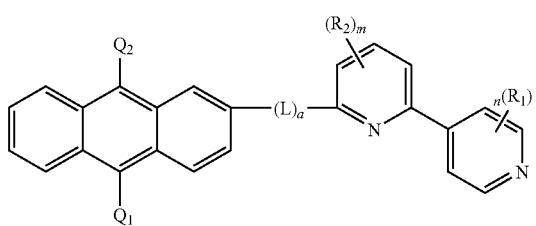

51
-continued

Formula 3b
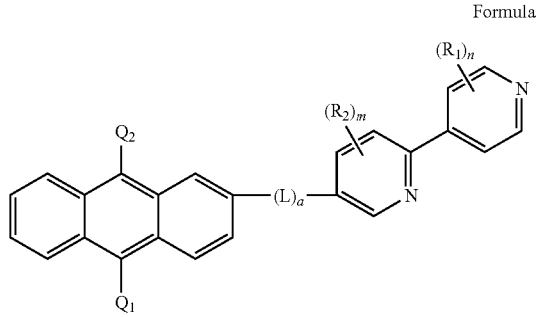

Formula 3e
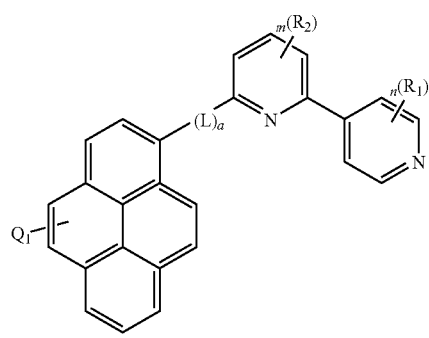

Formula 3f
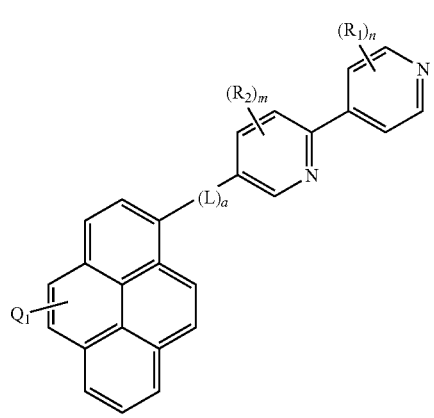

Formula 3g
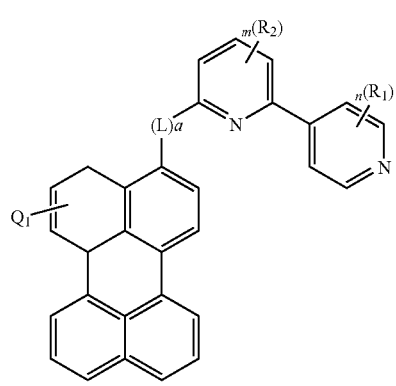

52
-continued

Formula 3h
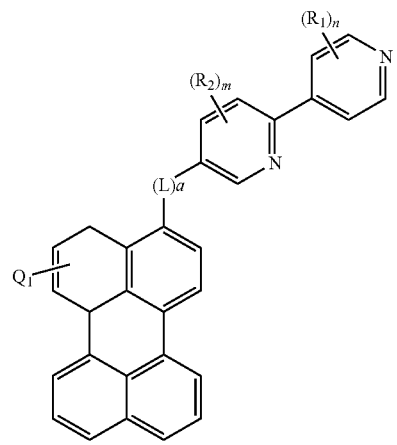

Formula 3i
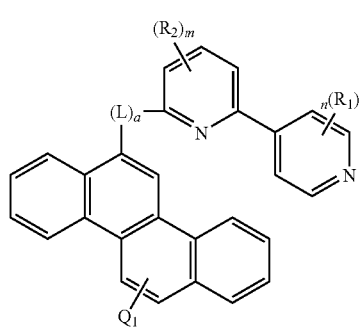

Formula 3j
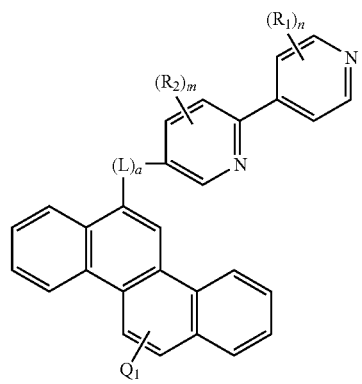

wherein:
each of $R_1$ and $R_2$ is independently selected from the group consisting of halogen atoms, hydroxy groups, cyano groups, substituted and unsubstituted $C_1$-$C_{30}$ alkyl groups, substituted and unsubstituted $C_1$-$C_{30}$ alkoxy groups, substituted and unsubstituted $C_2$-$C_{30}$ alkenyl groups, substituted and unsubstituted $C_6$-$C_{30}$ aryl groups, and substituted and unsubstituted $C_3$-$C_{30}$ heteroaryl groups;

n is an integer ranging from 0 to 4;

m is an integer ranging from 0 to 3;

L is selected from the group consisting of substituted and unsubstituted $C_6$-$C_{30}$ arylene groups, and substituted and unsubstituted $C_3$-$C_{30}$ heteroarylene groups;

a is an integer ranging from 0 to 5; and each of $Q_1$ and $Q_2$ is independently selected from the group consisting of halogen atoms, cyano groups, hydroxyl groups, $C_1$-$C_{10}$ alkyl groups, $C_1$-$C_{10}$ alkoxy groups, phenyl groups, phenyl groups substituted with at least one $C_1$-$C_{10}$ alkyl group or at least one $C_6$-$C_{12}$ aryl group, naphthyl groups, naphthyl groups substituted with at least one $C_1$-$C_{10}$ alkyl group or at least one $C_6$-$C_{12}$ aryl group, anthracenyl groups, anthracenyl groups substituted with at least one $C_1$-$C_{10}$ alkyl group or at least one $C_6$-$C_{12}$ aryl group, fluorenyl groups, fluorenyl groups substituted with at least one $C_1$-$C_{10}$ alkyl group or at least one $C_6$-$C_{12}$ aryl group, phenanthrenyl groups, phenanthrenyl groups substituted with at least one $C_1$-$C_{10}$ alkyl group or at least one $C_6$-$C_{12}$ aryl group, pyrenyl groups, pyrenyl groups substituted with at least one $C_1$-$C_{10}$ alkyl group or at least one $C_6$-$C_{12}$ aryl group, fluoranthrenyl groups, and fluoranthrenyl groups substituted with at least one $C_1$-$C_{10}$ alkyl group or at least one $C_6$-$C_{12}$ aryl group.

11. The bipyridine-based compound of claim 1, wherein the bipyridine-based compound is selected from the group consisting of Compounds 1 to 27:

Compound 1

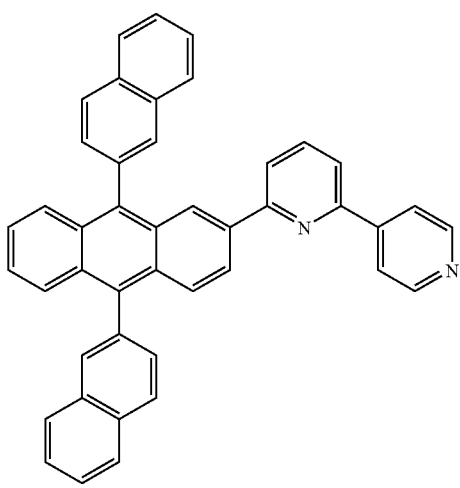

Compound 2

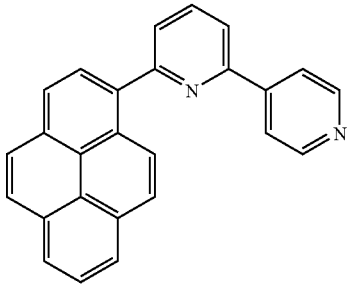

Compound 3

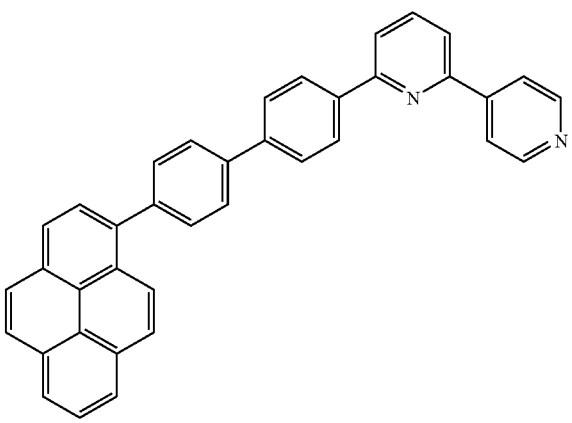

Compound 4

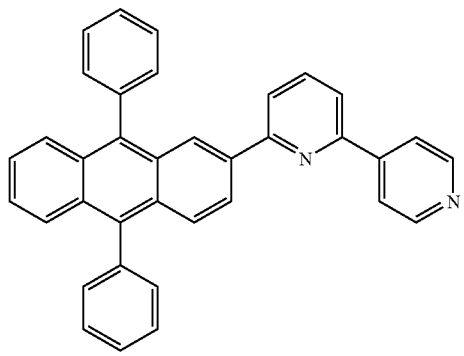

Compound 5

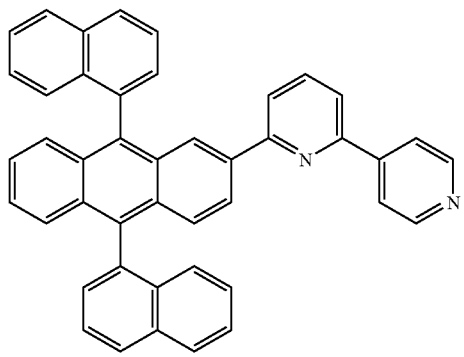

Compound 6

Compound 7
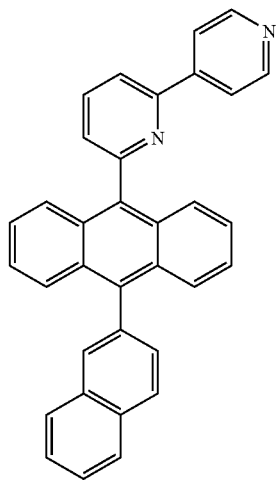
Compound 8
Compound 9
Compound 10
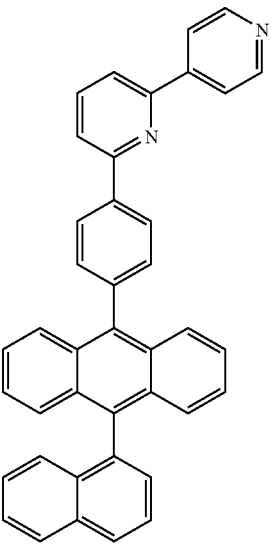
Compound 11
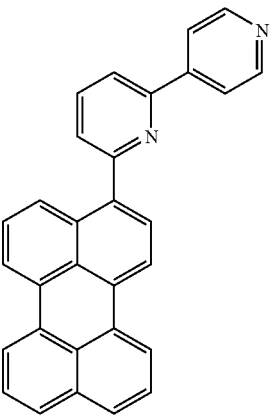
Compound 12
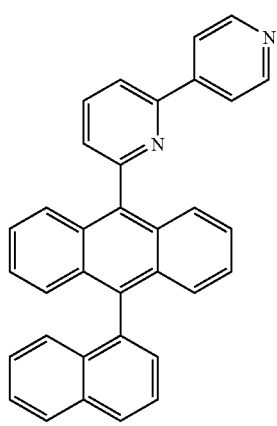
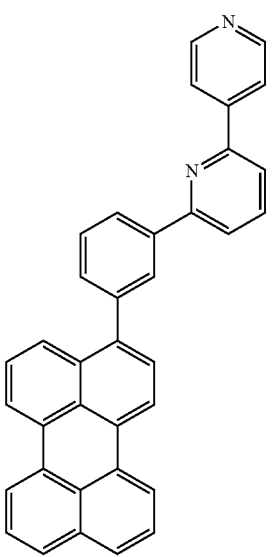

Compound 13
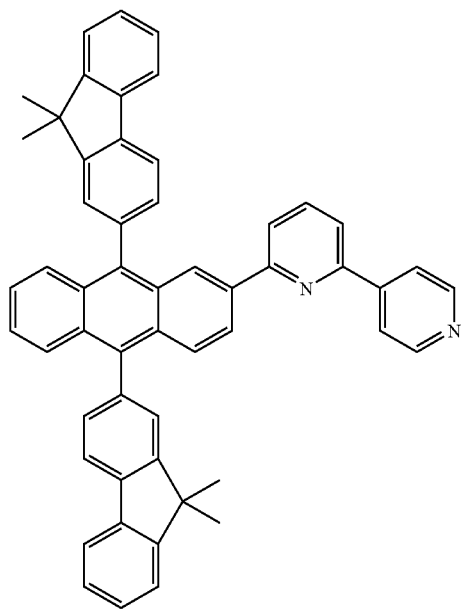
Compound 14
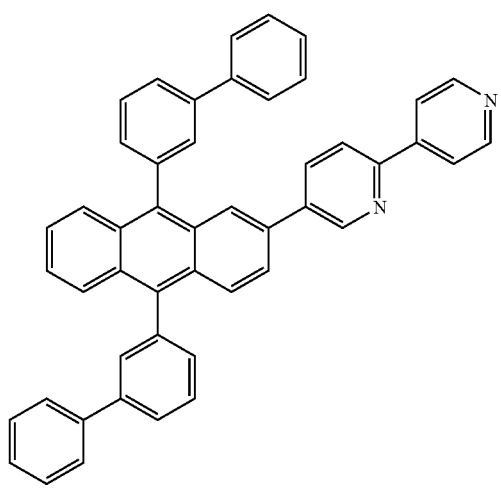
Compound 15
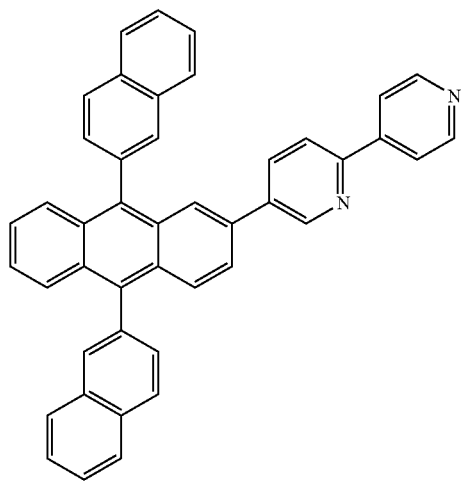
Compound 16
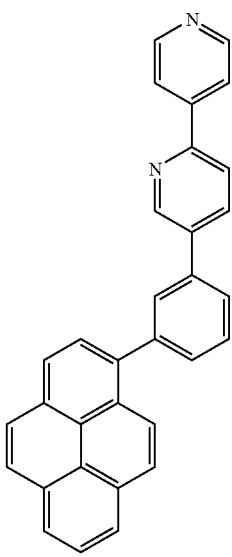
Compound 17
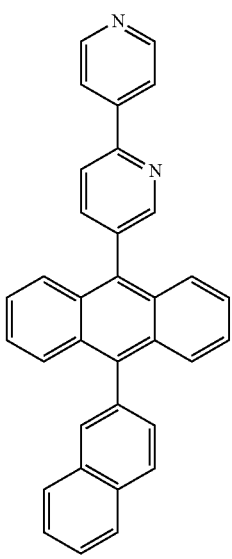
Compound 18
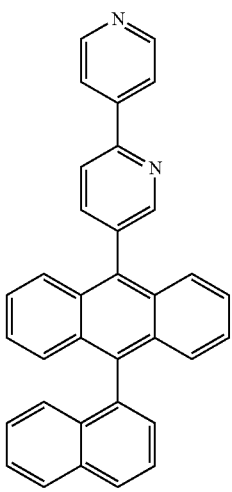

Compound 19
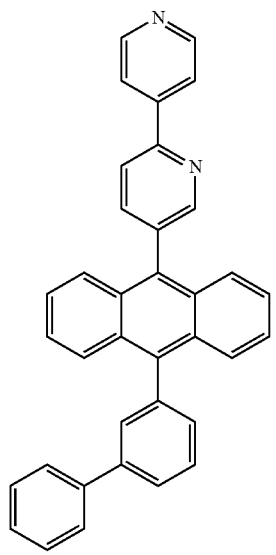
Compound 20
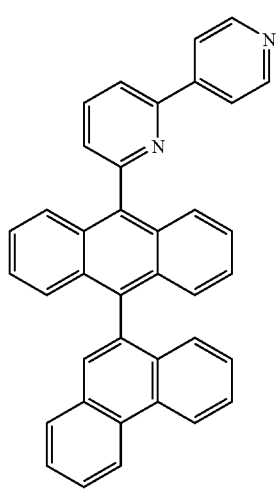
Compound 21
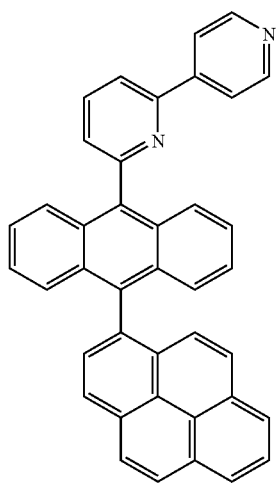
Compound 22
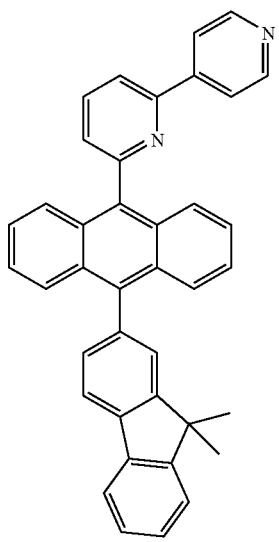
Compound 23
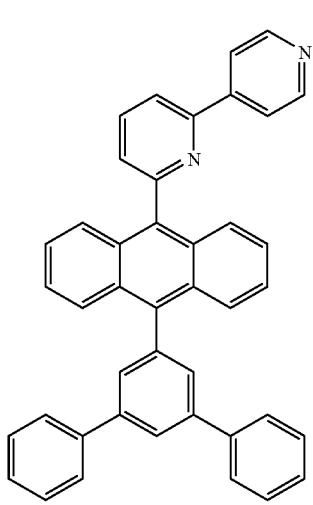
Compound 24
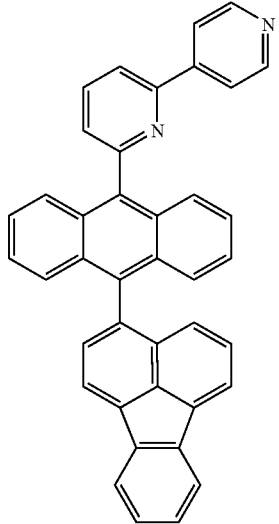

Compound 25

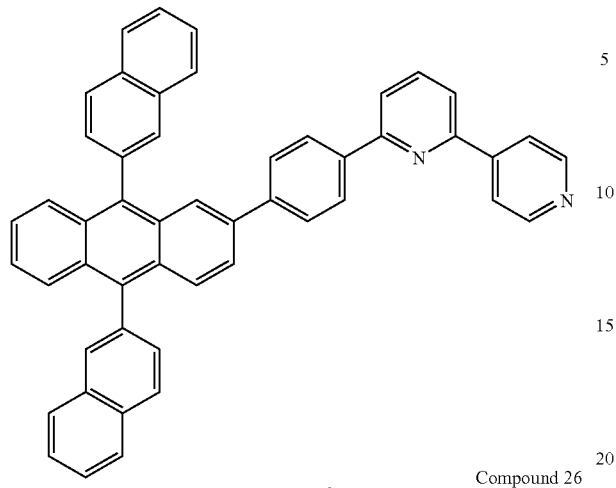

Compound 26

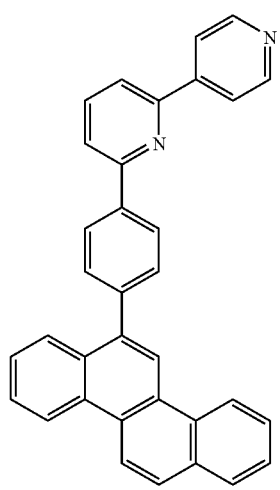

Compound 27

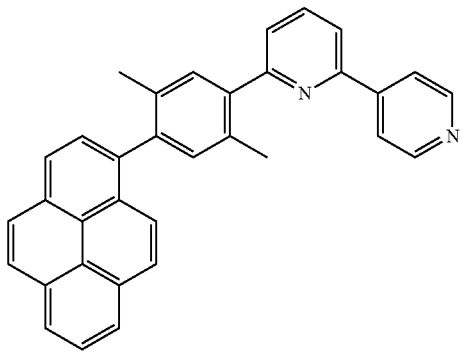

12. An organic light emitting diode (OLED) comprising:
   a first electrode;
   a second electrode; and
   an organic layer comprising the bipyridine-based compound according to claim 1.

13. The OLED of claim 12, wherein the organic layer is an electron transport layer.

14. The OLED of claim 13, further comprising at least one layer selected from the group consisting of hole injection layers, hole transport layers, emitting layers, hole blocking layers, and electron injection layers.

* * * * *